(12) United States Patent
Averback

(10) Patent No.: US 7,572,450 B2
(45) Date of Patent: *Aug. 11, 2009

(54) COMPOSITION FOR PREVENTING CELL DEATH AND/OR TISSUE NECROSIS RESULTING FROM CONTACT WITH NEURAL THREAD PROTEINS

(75) Inventor: Paul A. Averback, Quebec (CA)

(73) Assignee: Nymox Corporation, St. Laurent, Quebec (CA)

( * ) Notice: Subject to any disclaimer, the term of this patent is extended or adjusted under 35 U.S.C. 154(b) by 1301 days.

This patent is subject to a terminal disclaimer.

(21) Appl. No.: 10/146,130

(22) Filed: May 16, 2002

(65) Prior Publication Data

US 2003/0004107 A1   Jan. 2, 2003

Related U.S. Application Data

(60) Provisional application No. 60/290,971, filed on May 16, 2001.

(51) Int. Cl.
*A61K 39/38* (2006.01)
*A61K 38/00* (2006.01)
*A61K 38/04* (2006.01)

(52) U.S. Cl. .................... 424/185.1; 530/300; 530/330

(58) Field of Classification Search ................. 530/300, 530/350, 402; 514/2
See application file for complete search history.

(56) References Cited

U.S. PATENT DOCUMENTS 5,830,670 A   11/1998   de la Monte et al.
5,948,634 A   9/1999    de la Monte et al.
5,948,888 A   9/1999    de la Monte et al.
6,071,705 A   6/2000    Wands et al.

FOREIGN PATENT DOCUMENTS

| WO | WO 94/23756  | 10/1994 |
| WO | WO 01/46237  | 6/2001  |
| WO | WO 01/46440  | 6/2001  |
| WO | WO 02/34915  | 5/2002  |
| WO | WO 02/074323 | 9/2002  |

OTHER PUBLICATIONS

Vukicevic et al., 1996, PNAS USA 93:9021-9026.*
Skolnick et al., Trends in Biotech., 18(1):34-39, 2000.*
Choh, PNAS 77(6):3211-14, 1990.*
Fitzpatrick et al., WO 200234915 May 2, 2002.*
Neuwelt, E. A., "Osmotic Blood-Brain Barrier Modification: Monoclonal Antibody, Albumin, and Methotrexate Delivery to Cerebrospinal Fluid and Brain", Neurosurgery, 17:419-423, 1985.*

* cited by examiner

*Primary Examiner*—Olga N Chernyshev
(74) *Attorney, Agent, or Firm*—Goodwin Procter LLP

(57) ABSTRACT

Disclosed is a method of preventing, inhibiting, and/or ameliorating cell death and/or tissue necrosis in live tissue by contacting live tissue with at least a segment of NTP, or homologue, variant, derivative or mimetic thereof, where the segment of NTP, or homologue, variant, derivative or mimetic thereof is present in an amount effective to prevent, inhibit, and/or ameliorate cell death and/or tissue necrosis. The method is capable of treating conditions requiring prevention, inhibition, and/or amelioration of cell death and/or tissue necrosis.

2 Claims, 9 Drawing Sheets

Figure 1

```
   1  tttttttttttgag ATG GAG TTT TCG CTC TTG TTG CCC AGG CTG GAG TGC AAT GGC GCA ATC   62
   1                 M   E   F   S   L   L   L   P   R   L   E   C   N   G   A   I    16

63  TCA GCT CAC CGC AAC CTC CGC CTC CCG GGT TCA AGC GAT TCT CCT GCC TCA GCC TCC CCA  122
  17  S   A   H   R   N   L   R   L   P   G   S   S   D   S   P   A   S   A   S   P    36

123  GTA GCT GGG ATT ACA GGC ATG TGC ACC CAC GCT CGG CTA ATT TTG TAT TTT TTT TTA GTA  182
  37  V   A   G   I   T   G   M   C   T   H   A   R   L   I   L   Y   F   F   L   V    56

183  GAG ATG GAG TTT CTC CAT GTT GGT CAG GCT GGT CTC GAA CTC CCG ACC TCA GAT GAT CCC  242
  57  E   M   E   F   L   H   V   G   Q   A   G   L   E   L   P   T   S   D   D   P    76

243  TCC GTC TCG GCC TCC CAA AGT GCT AGA TAC AGG ACT GGC CAC CAT GCC CGG CTC TGC CTG  302
  77  S   V   S   A   S   Q   S   A   R   Y   R   T   G   H   H   A   R   L   C   L    96

303  GCT AAT TTT TGT GGT AGA AAC AGG GTT TCA CTG ATG TGC CCA AGC TGG TCT CCT GAG CTC  362
  97  A   N   F   C   G   R   N   R   V   S   L   M   C   P   S   W   S   P   E   L   116

363  AAG CAG TCC ACC TGC CTC AGC CTC CCA AAG TGC TGG GAT TAC AGG CGT GCA GCC GTG CCT  422
 117  K   Q   S   T   C   L   S   L   P   K   C   W   D   Y   R   R   A   A   V   P   136

423  GGC CTT TTT ATT TTA TTT TTT TTA AGA CAC AGG TGT CCC ACT CTT ACC CAG GAT GAA GTG  482
 137  G   L   F   I   L   F   F   L   R   H   R   C   P   T   L   T   Q   D   E   V   156

483  CAG TGG TGT GAT CAC AGC TCA CTG CAG CCT TCA ACT CCT GAG ATC AAG CAT CCT CCT GCC  542
 157  Q   W   C   D   H   S   S   L   Q   P   S   T   P   E   I   K   H   P   P   A   176

543  TCA GCC TCC CAA GTA GCT GGG ACC AAA GAC ATG CAC CAC TAC ACC TGG CTA ATT TTT ATT  602
 177  S   A   S   Q   V   A   G   T   K   D   M   H   H   Y   T   W   L   I   F   I   196

603  TTT ATT TTT AAT TTT TTG AGA CAG AGT CTC AAC TCT GTC ACC CAG GCT GGA GTG CAG TGG  662
 197  F   I   F   N   F   L   R   Q   S   L   N   S   V   T   Q   A   G   V   Q   W   216

663  CGC AAT CTT GGC TCA CTG CAA CCT CTG CCT CCC GGG TTC AAG TTA TTC TCC TGC CCC AGC  722
 217  R   N   L   G   S   L   Q   P   L   P   P   G   F   K   L   F   S   C   P   S   236

723  CTC CTG AGT AGC TGG GAC TAC AGG CGC CCA CCA CGC CTA GCT AAT TTT TTT GTA TTT TTA  782
 237  L   L   S   S   W   D   Y   R   R   P   P   R   L   A   N   F   F   V   F   L   256

783  GTA GAG ATG GGG TTC ACC ATG TTC GCC AGG TTG ATC TTG ATC TCT GGA CCT TGT GAT CTG  842
 257  V   E   M   G   F   T   M   F   A   R   L   I   L   I   S   G   P   C   D   L   276

843  CCT GCC TCG GCC TCC CAA AGT GCT GGG ATT ACA GGC GTG AGC CAC CAC GCC CGG CTT ATT  902
 277  P   A   S   A   S   Q   S   A   G   I   T   G   V   S   H   H   A   R   L   I   296

903  TTT AAT TTT TGT TTG TTT GAA ATG GAA TCT CAC TCT GTT ACC CAG GCT GGA GTG CAA TGG  962
 297  F   N   F   C   L   F   E   M   E   S   H   S   V   T   Q   A   G   V   Q   W   316

963  CCA AAT CTC GGC TCA CTG CAA CCT CTG CCT CCC GGG CTC AAG CGA TTC TCC TGT CTC AGC 1022
 317  P   N   L   G   S   L   Q   P   L   P   P   G   L   K   R   F   S   C   L   S   336

1023  CTC CCA AGC AGC TGG GAT TAC GGG CAC CTG CCA CCA CAC CCC GCT AAT TTT TGT ATT TTC 1082
 337  L   P   S   S   W   D   Y   G   H   L   P   P   H   P   A   N   F   C   I   F   356

1083  ATT AGA GGC GGG GTT TCA CCA TAT TTG TCA GGC TGG TCT CAA ACT CCT GAC CTC AGG tgac 1143
 357  I   R   G   G   V   S   P   Y   L   S   G   W   S   Q   T   P   D   L   R       375

1144  ccacctgcctcagccttccaaagtgctgggattacaggcgtgagccacctcacccagccggctaatttagataaaaaaat 1223
1224  atgtagcaatgggggtcttgctatgttgcccaggctggtctcaaacttctggcttcatgcaatccttccaaatgagcca 1303
1304  caacacccagccagtcacattttttaaacagttacatctttattttagtatactagaaagtaatacaataaacatgtcaa 1383
1384  acctgcaaattcagtagtaacagagttctttttataactttttaaacaaagctttagagca                    1442
```

Figure 2

NTP[122]

```
1    Met-Met-Val-Cys-Trp-Asn-Arg-Phe-Gly-Lys-
     M   M   V   C   W   N   R   F   G   K

11   Trp-Val-Tyr-Phe-Ile-Ser-Ala-Ile-Phe-Asn-
     W   V   Y   F   I   S   A   I   F   N

21   Phe-Gly-Pro-Arg-Tyr-Leu-Tyr-His-Gly-Val-
     F   G   P   R   Y   L   Y   H   G   V

31   Pro-Phe-Tyr-Phe-Leu-Ile-Leu-Val-Arg-Ile-
     P   F   Y   F   L   I   L   V   R   I

41   Ile-Ser-Phe-Leu-Ile-Gly-Asp-Met-Glu-Asp-
     I   S   F   L   I   G   D   M   E   D

51   Val-Leu-Leu-Asn-Cys-Thr-Leu-Leu-Lys-Arg-
     V   L   L   N   C   T   L   L   K   R

61   Ser-Ser-Arg-Phe-Arg-Phe-Trp-Gly-Ala-Leu-
     S   S   R   F   R   F   W   G   A   L

71   Val-Cys-Ser-Met-Asp-Ser-Cys-Arg-Phe-Ser
     V   C   S   M   D   S   C   R   F   S

81   Arg-Val-Ala-Val-Thr-Tyr-Arg-Phe-Ile-Thr-
     R   V   A   V   T   Y   R   F   I   T

91   Leu-Leu-Asn-Ile-Pro-Ser-Pro-Ala-Val-Trp-
     L   L   N   I   P   S   P   A   V   W

101  Met-Ala-Arg-Asn-Thr-Ile-Asp-Gln-Gln-Val-
     M   A   R   N   T   I   D   Q   Q   V

111  Leu-Ser-Arg-Ile-Lys-Leu-Glu-Ile-Lys-Arg-
     L   S   R   I   K   L   E   I   K   R

121  Cys-Leu
     C   L
```

Figure 3

NTP[112]

| | | |
|---|---|---|
| 1 | Met-Ala-Gln-Ser-Arg-Leu-Thr-Ala-The-Ser- | |
| | M   A   Q   S   R   L   T   A   T   S | |
| 11 | Ala-Ser-Arg-Val-Gln-Ala-Ile-Leu-Leu-Ser- | |
| | A   S   R   V   Q   A   I   L   L   S | |
| 21 | Gln-Pro-Pro-Lys-Gln-Leu-Gly-Leu-Arg-Ala- | |
| | Q   P   P   K   Q   L   G   L   R   A | |
| 31 | Pro-Ala-Asn-Thr-Pro-Leu-Ile-Phe-Val-Phe- | |
| | P   A   N   T   P   L   I   F   V   F | |
| 41 | Ser-Leu-Glu-Ala-Gly-Phe-His-His-Ile-Cys- | |
| | S   L   E   A   G   F   H   H   I   C | |
| 51 | Gln-Ala-Gly-Leu-Lys-Leu-Leu-Thr-Ser-Gly- | |
| | Q   A   G   L   K   L   L   T   S   G | |
| 61 | Asp-Pro-Pro-Ala-Ser-Ala-Phe-Gln-Ser-Ala- | |
| | D   P   P   A   S   A   F   Q   S   A | |
| 71 | Gly-Ile-Thr-Gly-Val-Ser-His-Leu-Thr-Gln- | |
| | G   I   T   G   V   S   H   L   T   Q | |
| 81 | Pro-Ala-Asn-Leu-Asp-Lys-Lys-Ile-Cys-Ser- | |
| | P   A   N   L   D   K   K   I   C   S | |
| 91 | Asn-Gly-Gly-Ser-Cys-Tyr-Val-Ala-Gln-Ala- | |
| | N   G   G   S   C   Y   V   A   Q   A | |
| 101 | Gly-Leu-Lys-Leu-Leu-Ala-Ser-Cys-Asn-Pro- | |
| | G   L   K   L   L   A   S   C   N   P | |
| 111 | Ser-Lys | |
| | S   K | |

Figure 4

NTP[106]

| | | | | | | | | | | |
|---|---|---|---|---|---|---|---|---|---|---|
| 1 | Met- | Trp- | Thr- | Leu- | Lys- | Ser- | Ser- | Leu- | Val- | Leu- |
| | M | W | T | L | K | S | S | L | V | L |
| 11 | Leu- | Leu- | Cys- | Leu- | Thr- | Cys- | Ser- | Tyr- | Ala- | Phe- |
| | L | L | C | L | T | C | S | Y | A | F |
| 21 | Met- | Phe- | Ser- | Ser- | Leu- | Arg- | Gln- | Lys- | Thr- | Ser- |
| | M | F | S | S | L | R | Q | K | T | S |
| 31 | Glu- | Pro- | Gln- | Gly- | Lys- | Val- | Pro- | Cys- | Gly- | Glu- |
| | E | P | Q | G | K | V | P | C | G | E |
| 41 | His- | Phe- | Arg- | Ile- | Arg- | Gln- | Asn- | Leu- | Pro- | Glu- |
| | H | F | R | I | R | Q | N | L | P | E |
| 51 | His- | Thr- | Gln- | Gly- | Trp- | Leu- | Gly- | Ser- | Lys- | Trp- |
| | H | T | Q | G | W | L | G | S | K | W |
| 61 | Leu- | Trp- | Leu- | Leu- | Phe- | Ala- | Val- | Val- | Pro- | Phe- |
| | L | W | L | L | F | A | V | V | P | F |
| 71 | Val- | Ile- | Leu- | Lys- | Cys- | Gln- | Arg- | Asp- | Ser- | Glu- |
| | V | I | L | K | C | Q | R | D | S | E |
| 81 | Lys- | Asn- | Lys- | Val- | Arg- | Met- | Ala- | Pro- | Phe- | Phe- |
| | K | N | K | V | R | M | A | P | F | F |
| 91 | Leu- | His- | His- | Ile- | Asp- | Ser- | Ile- | Ser- | Gly- | Val- |
| | L | H | H | I | D | S | I | S | G | V |
| 101 | Ser- | Gly- | Lys- | Arg- | Met- | Phe | | | | |
| | S | G | K | R | M | F | | | | |

Figure 5

NTP [106]

| | | | | | | | | | | |
|---|---|---|---|---|---|---|---|---|---|---|
| 1 | Met- | Phe- | Phe- | Val- | Leu- | Tyr- | Arg- | Phe- | Cys- | Phe- |
| | M | F | F | V | L | Y | R | F | C | F |
| 11 | Cys- | Phe- | Phe- | Glu- | Thr- | Glu- | Ser- | His- | Ser- | Leu- |
| | C | F | F | E | T | E | S | H | S | L |
| 21 | Thr- | Gln- | Ala- | Gly- | Val- | Gln- | Trp- | Cys- | Glu- | Leu- |
| | T | Q | A | G | V | Q | W | C | E | L |
| 31 | Gly- | Ser- | Pro- | Gln- | Pro- | Leu- | Pro- | Ser- | Gly- | Phe- |
| | G | S | P | Q | P | L | P | S | G | F |
| 41 | Lys- | Arg- | Phe- | Ser- | Cys- | Leu- | Ser- | Leu- | Leu- | Ser- |
| | K | R | F | S | C | L | S | L | L | S |
| 51 | Ser- | Trp- | Asp- | Tyr- | Ser- | His- | Glu- | Pro- | Pro- | His- |
| | S | W | D | Y | S | H | E | P | P | H |
| 61 | Pro- | Val- | Ile- | Cys- | Ser- | Phe- | Leu- | Met- | Glu- | Lys- |
| | P | V | I | C | S | F | L | M | E | K |
| 71 | Cys- | Leu- | Ile- | Leu- | Tyr- | Lys- | Pro- | Asn- | Gly- | Asp- |
| | C | L | I | L | Y | K | P | N | G | D |
| 81 | Thr- | Ile- | Gly- | Pro- | Ile- | Leu- | Val- | Gln- | Gln- | Gly- |
| | T | I | G | P | I | L | V | Q | Q | G |
| 91 | Lys- | Arg- | Gln- | Lys- | Leu- | Tyr- | Ile- | Ser- | Ala- | Asp- |
| | K | R | Q | K | L | Y | I | S | A | D |
| 100 | Leu- | Val- | His- | Leu- | Ile- | Ala | | | | |
| | L | V | H | L | I | A | | | | |

Figure 6

NTP[98]

| | |
|---|---|
| 1 | Glu-Ala-Tyr-Tyr-Thr-Met-Leu-His-Leu-Pro-<br>E   A   Y   Y   T   M   L   H   L   P |
| 11 | Thr-Thr-Asn-Arg-Pro-Lys-Ile-Ala-His-Cys<br>T   T   N   R   P   K   I   A   H   C |
| 21 | Ile-Leu-Phe-Asn-Gln-Pro-His-Ser-Pro-Arg-<br>I   L   F   N   Q   P   H   S   P   R |
| 31 | Ser-Asn-Ser-His-Ser-His-Pro-Asn-Pro-Leu-<br>S   N   S   H   S   H   P   N   P   L |
| 41 | Lys-Leu-His-Arg-Arg-Ser-His-Ser-His-Asn-<br>K   L   H   R   R   S   H   S   H   N |
| 51 | Arg-Pro-Arg-Ala-Tyr-Ile-Leu-Ile-Thr-Ile-<br>R   P   R   A   Y   I   L   I   T   I |
| 61 | Leu-Pro-Ser-Lys-Leu-Lys-Leu-Arg-Thr-His-<br>L   P   S   K   L   K   L   R   T   H |
| 71 | Ser-Gln-Ser-His-His-Asn-Pro-Leu-Ser-Arg-<br>S   Q   S   H   H   N   P   L   S   R |
| 81 | Thr-Ser-Asn-Ser-Thr-Pro-Thr-Asn-Ser-Phe-<br>T   S   N   S   T   P   T   N   S   F |
| 91 | Leu-Met-Thr-Ser-Ser-Lys-Pro-Arg<br>L   M   T   S   S   K   P   R |

Figure 7

NTP[75]

```
1    Ser-Ser-Ser-Leu-Gly-Leu-Pro-Lys-Cys-Trp-
      S   S   S   L   G   L   P   K   C   W

11   Asp-Tyr-Arg-His-Glu-Leu-Leu-Ser-Leu-Ala-
      D   Y   R   H   E   L   L   S   L   A

21   Leu-Met-Ile-Asn-Phe-Arg-Val-Met-Ala-Cys
      L   M   I   N   F   R   V   M   A   C

31   Thr-Phe-Lys-Gln-His-Ile-Glu-Leu-Arg-Gln-
      T   F   K   Q   H   I   E   L   R   Q

41   Lys-Ile-Ser-Ile-Val-Pro-Arg-Lys-Leu-Cys-
      K   I   S   I   V   P   R   K   L   C

51   Cys-Met-Gly-Pro-Val-Cys-Pro-Val-Lys-Ile-
      C   M   G   P   V   C   P   V   K   I

61   Ala-Leu-Leu-Thr-Ile-Asn-Gly-His-Cys-Thr-
      A   L   L   T   I   N   G   H   C   T

71   Trp-Leu-Pro-Ala-Ser
      W   L   P   A   S
```

Figure 8

NTP[68]

```
1    Met-Phe-Val-Phe-Cys-Leu-Ile-Leu-Asn-Arg-
      M   F   V   F   C   L   I   L   N   R

11   Glu-Lys-Ile-Lys-Gly-Gly-Asn-Ser-Ser-Phe-
      E   K   I   K   G   G   N   S   S   F

21   Phe-Leu-Leu-Ser-Phe-Phe-Phe-Ser-Phe-Gln-
      F   L   L   S   F   F   F   S   F   Q

31   Asn-Cys-Cys-Gln-Cys-Phe-Gln-Cys-Arg-Thr-
      N   C   C   Q   C   F   Q   C   R   T

41   Thr-Glu-Gly-Tyr-Ala-Val-Glu-Cys-Phe-Tyr-
      T   E   G   Y   A   V   E   C   F   Y

51   Cys-Leu-Val-Asp-Lys-Ala-Ala-Phe-Glu-Cys-
      C   L   V   D   K   A   A   F   E   C

61   Trp-Trp-Phe-Tyr-Ser-Phe-Asp-Thr
      W   W   F   Y   S   F   D   T
```

Figure 9

NTP[61]

```
1    Met-Glu-Pro-His-Thr-Val-Ala-Gln-Ala-Gly-
     M   E   P   H   T   V   A   Q   A   G

11   Val-Pro-Gln-His-Asp-Leu-Gly-Ser-Leu-Gln-
     V   P   Q   H   D   L   G   S   L   Q

21   Ser-Leu-Leu-Pro-Arg-Phe-Lys-Arg-Phe-Ser-
     S   L   L   P   R   F   K   R   F   S

31   Cys-Leu-Ile-Leu-Pro-Lys-Ile-Trp-Asp-Tyr-
     C   L   I   L   P   K   I   W   D   Y

41   Arg-Asn-Met-Asn-Thr-Ala-Leu-Ile-Lys-Arg-
     R   N   M   N   T   A   L   I   K   R

51   Asn-Arg-Tyr-Thr-Pro-Glu-Thr-Gly-Arg-Lys-
     N   R   Y   T   P   E   T   G   R   K

61   Ser
     S
```

US 7,572,450 B2

SEQUENCE LISTING

```
<160> NUMBER OF SEQ ID NOS: 43

<210> SEQ ID NO 1
<211> LENGTH: 1442
<212> TYPE: DNA
<213> ORGANISM: Homo sapiens
<220> FEATURE:
<221> NAME/KEY: CDS
<222> LOCATION: (15)..(1139)

<400> SEQUENCE: 1
tttttttttt tgag atg gag ttt tcg ctc ttg ttg ccc agg ctg gag tgc      50
            Met Glu Phe Ser Leu Leu Leu Pro Arg Leu Glu Cys
              1               5                  10 aat ggc gca atc tca gct cac cgc aac ctc cgc ctc ccg ggt tca agc      98
Asn Gly Ala Ile Ser Ala His Arg Asn Leu Arg Leu Pro Gly Ser Ser
        15                  20                  25 gat tct cct gcc tca gcc tcc cca gta gct ggg att aca ggc atg tgc     146
Asp Ser Pro Ala Ser Ala Ser Pro Val Ala Gly Ile Thr Gly Met Cys
    30                  35                  40 acc cac gct cgg cta att ttg tat ttt tta gta gag atg gag ttt         194
Thr His Ala Arg Leu Ile Leu Tyr Phe Phe Leu Val Glu Met Glu Phe
 45                  50                  55                  60 ctc cat gtt ggt cag gct ggt ctc gaa ctc ccg acc tca gat gat ccc     242
Leu His Val Gly Gln Ala Gly Leu Glu Leu Pro Thr Ser Asp Asp Pro
                65                  70                  75 tcc gtc tcg gcc tcc caa agt gct aga tac agg act ggc cac cat gcc     290
Ser Val Ser Ala Ser Gln Ser Ala Arg Tyr Arg Thr Gly His His Ala
            80                  85                  90 cgg ctc tgc ctg gct aat ttt tgt ggt aga aac agg gtt tca ctg atg     338
Arg Leu Cys Leu Ala Asn Phe Cys Gly Arg Asn Arg Val Ser Leu Met
        95                 100                 105 tgc cca agc tgg tct cct gag ctc aag cag tcc acc tgc ctc agc ctc     386
Cys Pro Ser Trp Ser Pro Glu Leu Lys Gln Ser Thr Cys Leu Ser Leu
    110                 115                 120 cca aag tgc tgg gat tac agg cgt gca gcc gtg cct ggc ctt ttt att     434
Pro Lys Cys Trp Asp Tyr Arg Arg Ala Ala Val Pro Gly Leu Phe Ile
125                 130                 135                 140 tta ttt ttt tta aga cac agg tgt ccc act ctt acc cag gat gaa gtg     482
Leu Phe Phe Leu Arg His Arg Cys Pro Thr Leu Thr Gln Asp Glu Val
                145                 150                 155 cag tgg tgt gat cac agc tca ctg cag cct tca act cct gag atc aag     530
Gln Trp Cys Asp His Ser Ser Leu Gln Pro Ser Thr Pro Glu Ile Lys
```

```
                160                 165                 170
cat cct cct gcc tca gcc tcc caa gta gct ggg acc aaa gac atg cac       578
His Pro Pro Ala Ser Ala Ser Gln Val Ala Gly Thr Lys Asp Met His
        175                 180                 185 cac tac acc tgg cta att ttt att ttt att ttt aat ttt ttg aga cag       626
His Tyr Thr Trp Leu Ile Phe Ile Phe Ile Phe Asn Phe Leu Arg Gln
190                 195                 200 agt ctc aac tct gtc acc cag gct gga gtg cag tgg cgc aat ctt ggc       674
Ser Leu Asn Ser Val Thr Gln Ala Gly Val Gln Trp Arg Asn Leu Gly
205                 210                 215                 220 tca ctg caa cct ctg cct ccc ggg ttc aag tta ttc tcc tgc ccc agc       722
Ser Leu Gln Pro Leu Pro Pro Gly Phe Lys Leu Phe Ser Cys Pro Ser
                225                 230                 235 ctc ctg agt agc tgg gac tac agg cgc cca cca cgc cta gct aat ttt       770
Leu Leu Ser Ser Trp Asp Tyr Arg Arg Pro Pro Arg Leu Ala Asn Phe
        240                 245                 250 ttt gta ttt tta gta gag atg ggg ttc acc atg ttc gcc agg ttg atc       818
Phe Val Phe Leu Val Glu Met Gly Phe Thr Met Phe Ala Arg Leu Ile
                255                 260                 265 ttg atc tct gga cct tgt gat ctg cct gcc tcg gcc tcc caa agt gct       866
Leu Ile Ser Gly Pro Cys Asp Leu Pro Ala Ser Ala Ser Gln Ser Ala
        270                 275                 280 ggg att aca ggc gtg agc cac cac gcc cgg ctt att ttt aat ttt tgt       914
Gly Ile Thr Gly Val Ser His His Ala Arg Leu Ile Phe Asn Phe Cys
285                 290                 295                 300 ttg ttt gaa atg gaa tct cac tct gtt acc cag gct gga gtg caa tgg       962
Leu Phe Glu Met Glu Ser His Ser Val Thr Gln Ala Gly Val Gln Trp
                305                 310                 315 cca aat ctc ggc tca ctg caa cct ctg cct ccc ggg ctc aag cga ttc      1010
Pro Asn Leu Gly Ser Leu Gln Pro Leu Pro Pro Gly Leu Lys Arg Phe
        320                 325                 330 tcc tgt ctc agc ctc cca agc agc tgg gat tac ggg cac ctg cca cca      1058
Ser Cys Leu Ser Leu Pro Ser Ser Trp Asp Tyr Gly His Leu Pro Pro
        335                 340                 345 cac ccc gct aat ttt tgt att ttc att aga ggc ggg gtt tca cca tat      1106
His Pro Ala Asn Phe Cys Ile Phe Ile Arg Gly Gly Val Ser Pro Tyr
350                 355                 360 ttg tca ggc tgg tct caa act cct gac ctc agg tgacccacct gcctcagcct    1159
Leu Ser Gly Trp Ser Gln Thr Pro Asp Leu Arg
365                 370                 375 tccaaagtgc tgggattaca ggcgtgagcc acctcaccca gccggctaat ttagataaaa    1219
aaatatgtag caatgggggg tcttgctatg ttgcccaggc tggtctcaaa cttctggctt    1279
catgcaatcc ttccaaatga gccacaacac ccagccagtc acattttta aacagttaca    1339 tctttatttt agtatactag aaagtaatac aataaacatg tcaaacctgc aaattcagta    1399
gtaacagagt tcttttataa cttttaaaca aagctttaga gca                      1442

<210> SEQ ID NO 2
<211> LENGTH: 375
<212> TYPE: PRT
<213> ORGANISM: Homo sapiens

<400> SEQUENCE: 2

Met Glu Phe Ser Leu Leu Leu Pro Arg Leu Glu Cys Asn Gly Ala Ile
1               5                   10                  15

Ser Ala His Arg Asn Leu Arg Leu Pro Gly Ser Ser Asp Ser Pro Ala
            20                  25                  30

Ser Ala Ser Pro Val Ala Gly Ile Thr Gly Met Cys Thr His Ala Arg
```

```
                35                  40                  45
Leu Ile Leu Tyr Phe Phe Leu Val Glu Met Glu Phe Leu His Val Gly
     50                  55                  60

Gln Ala Gly Leu Glu Leu Pro Thr Ser Asp Pro Ser Val Ser Ala
 65                  70                  75                  80

Ser Gln Ser Ala Arg Tyr Arg Thr Gly His His Ala Arg Leu Cys Leu
                 85                  90                  95

Ala Asn Phe Cys Gly Arg Asn Arg Val Ser Leu Met Cys Pro Ser Trp
                100                 105                 110

Ser Pro Glu Leu Lys Gln Ser Thr Cys Leu Ser Leu Pro Lys Cys Trp
            115                 120                 125

Asp Tyr Arg Arg Ala Ala Val Pro Gly Leu Phe Ile Leu Phe Phe Leu
        130                 135                 140

Arg His Arg Cys Pro Thr Leu Thr Gln Asp Glu Val Gln Trp Cys Asp
145                 150                 155                 160

His Ser Ser Leu Gln Pro Ser Thr Pro Glu Ile Lys His Pro Pro Ala
                165                 170                 175

Ser Ala Ser Gln Val Ala Gly Thr Lys Asp Met His His Tyr Thr Trp
            180                 185                 190

Leu Ile Phe Ile Phe Ile Phe Asn Phe Leu Arg Gln Ser Leu Asn Ser
        195                 200                 205

Val Thr Gln Ala Gly Val Gln Trp Arg Asn Leu Gly Ser Leu Gln Pro
    210                 215                 220

Leu Pro Pro Gly Phe Lys Leu Phe Ser Cys Pro Ser Leu Leu Ser Ser
225                 230                 235                 240

Trp Asp Tyr Arg Arg Pro Pro Arg Leu Ala Asn Phe Phe Val Phe Leu
                245                 250                 255

Val Glu Met Gly Phe Thr Met Phe Ala Arg Leu Ile Leu Ile Ser Gly
            260                 265                 270

Pro Cys Asp Leu Pro Ala Ser Ala Ser Gln Ser Ala Gly Ile Thr Gly
        275                 280                 285

Val Ser His His Ala Arg Leu Ile Phe Asn Phe Cys Leu Phe Glu Met
    290                 295                 300

Glu Ser His Ser Val Thr Gln Ala Gly Val Gln Trp Pro Asn Leu Gly
305                 310                 315                 320

Ser Leu Gln Pro Leu Pro Pro Gly Leu Lys Arg Phe Ser Cys Leu Ser
                325                 330                 335

Leu Pro Ser Ser Trp Asp Tyr Gly His Leu Pro Pro His Pro Ala Asn
            340                 345                 350

Phe Cys Ile Phe Ile Arg Gly Gly Val Ser Pro Tyr Leu Ser Gly Trp
        355                 360                 365

Ser Gln Thr Pro Asp Leu Arg
    370                 375

<210> SEQ ID NO 3
<211> LENGTH: 122
<212> TYPE: PRT
<213> ORGANISM: Homo sapiens

<400> SEQUENCE: 3

Met Met Val Cys Trp Asn Arg Phe Gly Lys Trp Val Tyr Phe Ile Ser
  1               5                  10                  15

Ala Ile Phe Asn Phe Gly Pro Arg Tyr Leu Tyr His Gly Val Pro Phe
                 20                  25                  30
```

```
Tyr Phe Leu Ile Leu Val Arg Ile Ile Ser Phe Leu Ile Gly Asp Met
            35                  40                  45

Glu Asp Val Leu Leu Asn Cys Thr Leu Leu Lys Arg Ser Ser Arg Phe
 50                  55                  60

Arg Phe Trp Gly Ala Leu Val Cys Ser Met Asp Ser Cys Arg Phe Ser
 65                  70                  75                  80

Arg Val Ala Val Thr Tyr Arg Phe Ile Thr Leu Leu Asn Ile Pro Ser
                 85                  90                  95

Pro Ala Val Trp Met Ala Arg Asn Thr Ile Asp Gln Gln Val Leu Ser
                100                 105                 110

Arg Ile Lys Leu Glu Ile Lys Arg Cys Leu
            115                 120

<210> SEQ ID NO 4
<211> LENGTH: 112
<212> TYPE: PRT
<213> ORGANISM: Homo sapiens

<400> SEQUENCE: 4

Met Ala Gln Ser Arg Leu Thr Ala Thr Ser Ala Ser Arg Val Gln Ala
 1               5                  10                  15

Ile Leu Leu Ser Gln Pro Pro Lys Gln Leu Gly Leu Arg Ala Pro Ala
                20                  25                  30

Asn Thr Pro Leu Ile Phe Val Phe Ser Leu Glu Ala Gly Phe His His
            35                  40                  45

Ile Cys Gln Ala Gly Leu Lys Leu Leu Thr Ser Gly Asp Pro Pro Ala
 50                  55                  60

Ser Ala Phe Gln Ser Ala Gly Ile Thr Gly Val Ser His Leu Thr Gln
 65                  70                  75                  80

Pro Ala Asn Leu Asp Lys Lys Ile Cys Ser Asn Gly Gly Ser Cys Tyr
                 85                  90                  95

Val Ala Gln Ala Gly Leu Lys Leu Leu Ala Ser Cys Asn Pro Ser Lys
                100                 105                 110

<210> SEQ ID NO 5
<211> LENGTH: 106
<212> TYPE: PRT
<213> ORGANISM: Homo sapiens

<400> SEQUENCE: 5

Met Trp Thr Leu Lys Ser Ser Leu Val Leu Leu Cys Leu Thr Cys
 1               5                  10                  15

Ser Tyr Ala Phe Met Phe Ser Ser Leu Arg Gln Lys Thr Ser Glu Pro
                20                  25                  30

Gln Gly Lys Val Pro Cys Gly Glu His Phe Arg Ile Arg Gln Asn Leu
            35                  40                  45

Pro Glu His Thr Gln Gly Trp Leu Gly Ser Lys Trp Leu Trp Leu Leu
 50                  55                  60

Phe Ala Val Val Pro Phe Val Ile Leu Lys Cys Gln Arg Asp Ser Glu
 65                  70                  75                  80

Lys Asn Lys Val Arg Met Ala Pro Phe Phe Leu His His Ile Asp Ser
                 85                  90                  95

Ile Ser Gly Val Ser Gly Lys Arg Met Phe
                100                 105

<210> SEQ ID NO 6
<211> LENGTH: 106
```

```
<212> TYPE: PRT
<213> ORGANISM: Homo sapiens

<400> SEQUENCE: 6

Met Phe Val Leu Tyr Arg Phe Cys Phe Cys Phe Glu Thr Glu
 1               5                  10                  15

Ser His Ser Leu Thr Gln Ala Gly Val Gln Trp Cys Glu Leu Gly Ser
                20                  25                  30

Pro Gln Pro Leu Pro Ser Gly Phe Lys Arg Phe Ser Cys Leu Ser Leu
            35                  40                  45

Leu Ser Ser Trp Asp Tyr Ser His Glu Pro His Pro Val Ile Cys
    50                  55                  60

Ser Phe Leu Met Glu Lys Cys Leu Ile Leu Tyr Lys Pro Asn Gly Asp
 65                  70                  75                  80

Thr Ile Gly Pro Ile Leu Val Gln Gln Gly Lys Arg Gln Lys Leu Tyr
                85                  90                  95

Ile Ser Ala Asp Leu Val His Leu Ile Ala
            100                 105

<210> SEQ ID NO 7
<211> LENGTH: 98
<212> TYPE: PRT
<213> ORGANISM: Homo sapiens

<400> SEQUENCE: 7

Glu Ala Tyr Tyr Thr Met Leu His Leu Pro Thr Thr Asn Arg Pro Lys
 1               5                  10                  15

Ile Ala His Cys Ile Leu Phe Asn Gln Pro His Ser Pro Arg Ser Asn
                20                  25                  30

Ser His Ser His Pro Asn Pro Leu Lys Leu His Arg Arg Ser His Ser
            35                  40                  45

His Asn Arg Pro Arg Ala Tyr Ile Leu Ile Thr Ile Leu Pro Ser Lys
 50                  55                  60

Leu Lys Leu Arg Thr His Ser Gln Ser His His Asn Pro Leu Ser Arg
 65                  70                  75                  80

Thr Ser Asn Ser Thr Pro Thr Asn Ser Phe Leu Met Thr Ser Ser Lys
                85                  90                  95

Pro Arg

<210> SEQ ID NO 8
<211> LENGTH: 75
<212> TYPE: PRT
<213> ORGANISM: Homo sapiens

<400> SEQUENCE: 8

Ser Ser Ser Leu Gly Leu Pro Lys Cys Trp Asp Tyr Arg His Glu Leu
 1               5                  10                  15

Leu Ser Leu Ala Leu Met Ile Asn Phe Arg Val Met Ala Cys Thr Phe
                20                  25                  30

Lys Gln His Ile Glu Leu Arg Gln Lys Ile Ser Ile Val Pro Arg Lys
            35                  40                  45

Leu Cys Cys Met Gly Pro Val Cys Pro Val Lys Ile Ala Leu Leu Thr
 50                  55                  60

Ile Asn Gly His Cys Thr Trp Leu Pro Ala Ser
 65                  70                  75

<210> SEQ ID NO 9
```

```
<211> LENGTH: 68
<212> TYPE: PRT
<213> ORGANISM: Homo sapiens

<400> SEQUENCE: 9

Met Phe Val Phe Cys Leu Ile Leu Asn Arg Glu Lys Ile Lys Gly Gly
 1               5                  10                  15

Asn Ser Ser Phe Phe Leu Leu Ser Phe Phe Ser Phe Gln Asn Cys
                20                  25                  30

Cys Gln Cys Phe Gln Cys Arg Thr Thr Glu Gly Tyr Ala Val Glu Cys
                35                  40                  45

Phe Tyr Cys Leu Val Asp Lys Ala Ala Phe Glu Cys Trp Trp Phe Tyr
            50                  55                  60

Ser Phe Asp Thr
 65

<210> SEQ ID NO 10
<211> LENGTH: 61
<212> TYPE: PRT
<213> ORGANISM: Homo sapiens

<400> SEQUENCE: 10

Met Glu Pro His Thr Val Ala Gln Ala Gly Val Pro Gln His Asp Leu
 1               5                  10                  15

Gly Ser Leu Gln Ser Leu Leu Pro Arg Phe Lys Arg Phe Ser Cys Leu
                20                  25                  30

Ile Leu Pro Lys Ile Trp Asp Tyr Arg Asn Met Asn Thr Ala Leu Ile
            35                  40                  45

Lys Arg Asn Arg Tyr Thr Pro Glu Thr Gly Arg Lys Ser
        50                  55                  60

<210> SEQ ID NO 11
<211> LENGTH: 7
<212> TYPE: PRT
<213> ORGANISM: Homo sapiens

<400> SEQUENCE: 11

Gly Ile Thr Gly Met Cys Thr
 1               5

<210> SEQ ID NO 12
<211> LENGTH: 18
<212> TYPE: PRT
<213> ORGANISM: Homo sapiens

<400> SEQUENCE: 12

Gly Ile Thr Gly Met Cys Thr His Ala Arg Leu Ile Leu Tyr Phe Phe
 1               5                  10                  15

Leu Val

<210> SEQ ID NO 13
<211> LENGTH: 5
<212> TYPE: PRT
<213> ORGANISM: Homo sapiens

<400> SEQUENCE: 13

Tyr Phe Phe Leu Val
 1               5

<210> SEQ ID NO 14
<211> LENGTH: 4
```

```
<212> TYPE: PRT
<213> ORGANISM: Homo sapiens

<400> SEQUENCE: 14

Ala Arg Cys Leu
  1

<210> SEQ ID NO 15
<211> LENGTH: 5
<212> TYPE: PRT
<213> ORGANISM: Homo sapiens

<400> SEQUENCE: 15

His His Ala Arg Leu
  1               5

<210> SEQ ID NO 16
<211> LENGTH: 4
<212> TYPE: PRT
<213> ORGANISM: Homo sapiens

<400> SEQUENCE: 16

His Ala Arg Leu
  1

<210> SEQ ID NO 17
<211> LENGTH: 5
<212> TYPE: PRT
<213> ORGANISM: Homo sapiens

<400> SEQUENCE: 17

His Ala Arg Leu Ile
  1               5

<210> SEQ ID NO 18
<211> LENGTH: 6
<212> TYPE: PRT
<213> ORGANISM: Homo sapiens

<400> SEQUENCE: 18

His Ala Arg Leu Ile Leu
  1               5

<210> SEQ ID NO 19
<211> LENGTH: 7
<212> TYPE: PRT
<213> ORGANISM: Homo sapiens

<400> SEQUENCE: 19

His His Ala Arg Leu Cys Leu
  1               5

<210> SEQ ID NO 20
<211> LENGTH: 5
<212> TYPE: PRT
<213> ORGANISM: Homo sapiens

<400> SEQUENCE: 20

Ala Arg Leu Ile Leu
  1               5

<210> SEQ ID NO 21
<211> LENGTH: 7
<212> TYPE: PRT
<213> ORGANISM: Homo sapiens
```

```
<400> SEQUENCE: 21

His His Ala Arg Leu Ile Phe
  1               5

<210> SEQ ID NO 22
<211> LENGTH: 7
<212> TYPE: PRT
<213> ORGANISM: Homo sapiens

<400> SEQUENCE: 22

Thr His Ala Arg Leu Ile Leu
  1               5

<210> SEQ ID NO 23
<211> LENGTH: 4
<212> TYPE: PRT
<213> ORGANISM: Homo sapiens

<400> SEQUENCE: 23

Ala Arg Leu Ile
  1

<210> SEQ ID NO 24
<211> LENGTH: 6
<212> TYPE: PRT
<213> ORGANISM: Homo sapiens

<400> SEQUENCE: 24

His Ala Arg Leu Cys Leu
  1               5

<210> SEQ ID NO 25
<211> LENGTH: 5
<212> TYPE: PRT
<213> ORGANISM: Homo sapiens

<400> SEQUENCE: 25

Ala Arg Leu Cys Leu
  1               5

<210> SEQ ID NO 26
<211> LENGTH: 4
<212> TYPE: PRT
<213> ORGANISM: Homo sapiens

<400> SEQUENCE: 26

Ala Arg Cys Leu
  1

<210> SEQ ID NO 27
<211> LENGTH: 7
<212> TYPE: PRT
<213> ORGANISM: Homo sapiens

<400> SEQUENCE: 27

Met Phe Ala Arg Leu Ile Leu
  1               5

<210> SEQ ID NO 28
<211> LENGTH: 6
<212> TYPE: PRT
<213> ORGANISM: Homo sapiens

<400> SEQUENCE: 28
```

Phe Ala Arg Leu Ile Leu
 1               5

<210> SEQ ID NO 29
<211> LENGTH: 5
<212> TYPE: PRT
<213> ORGANISM: Homo sapiens

<400> SEQUENCE: 29

Phe Ala Arg Leu Ile
 1               5

<210> SEQ ID NO 30
<211> LENGTH: 4
<212> TYPE: PRT
<213> ORGANISM: Homo sapiens

<400> SEQUENCE: 30

Phe Ala Arg Leu
 1

<210> SEQ ID NO 31
<211> LENGTH: 6
<212> TYPE: PRT
<213> ORGANISM: Homo sapiens

<400> SEQUENCE: 31

His Ala Arg Leu Ile Phe
 1               5

<210> SEQ ID NO 32
<211> LENGTH: 5
<212> TYPE: PRT
<213> ORGANISM: Homo sapiens

<400> SEQUENCE: 32

Ala Arg Leu Ile Phe
 1               5

<210> SEQ ID NO 33
<211> LENGTH: 16
<212> TYPE: PRT
<213> ORGANISM: Homo sapiens

<400> SEQUENCE: 33

Leu His Ala Arg Leu Cys Leu Ala Asn Phe Cys Gly Arg Asn Arg Val
 1               5                  10                  15

<210> SEQ ID NO 34
<211> LENGTH: 15
<212> TYPE: PRT
<213> ORGANISM: Homo sapiens

<400> SEQUENCE: 34

Leu Ala Arg Leu Cys Leu Ala Asn Phe Cys Gly Asn Asn Asn Val
 1               5                  10                  15

<210> SEQ ID NO 35
<211> LENGTH: 13
<212> TYPE: PRT
<213> ORGANISM: Homo sapiens

<400> SEQUENCE: 35

Cys Ala Arg Tyr Arg Thr Gly His His Ala Arg Leu Met

```
                1               5                  10

<210> SEQ ID NO 36
<211> LENGTH: 12
<212> TYPE: PRT
<213> ORGANISM: Homo sapiens

<400> SEQUENCE: 36

His His Ala Arg Leu Pro Leu Ala Asn Phe Cys Gly
 1               5                  10

<210> SEQ ID NO 37
<211> LENGTH: 14
<212> TYPE: PRT
<213> ORGANISM: Homo sapiens

<400> SEQUENCE: 37

Arg Thr Gly His His Ala Arg Leu Cys Leu Ala Asn Phe Cys
 1               5                  10

<210> SEQ ID NO 38
<211> LENGTH: 15
<212> TYPE: PRT
<213> ORGANISM: Homo sapiens

<400> SEQUENCE: 38

Cys Glu Ser Ala Arg Tyr Arg Thr Gly His His Ala Arg Leu Cys
 1               5                  10                  15

<210> SEQ ID NO 39
<211> LENGTH: 10
<212> TYPE: PRT
<213> ORGANISM: Homo sapiens

<400> SEQUENCE: 39

Asp Asn Thr His His Ala Arg Leu Ile Leu
 1               5                  10

<210> SEQ ID NO 40
<211> LENGTH: 8
<212> TYPE: PRT
<213> ORGANISM: Homo sapiens

<400> SEQUENCE: 40

Ser His His Ala Arg Leu Ile Leu
 1               5

<210> SEQ ID NO 41
<211> LENGTH: 6
<212> TYPE: PRT
<213> ORGANISM: Homo sapiens

<400> SEQUENCE: 41

His Ala Arg Leu Met Leu
 1               5

<210> SEQ ID NO 42
<211> LENGTH: 6
<212> TYPE: PRT
<213> ORGANISM: Homo sapiens

<400> SEQUENCE: 42

His Ala Arg Leu Val Leu
 1               5
```

```
-continued

<210> SEQ ID NO 43
<211> LENGTH: 6
<212> TYPE: PRT
<213> ORGANISM: Homo sapiens

<400> SEQUENCE: 43

His Ala Lys Leu Ile Leu
 1               5
```

COMPOSITION FOR PREVENTING CELL DEATH AND/OR TISSUE NECROSIS RESULTING FROM CONTACT WITH NEURAL THREAD PROTEINS

This application claims priority to U.S. Provisional Patent Application No. 60/290,971, filed May 16, 2001, entitled: "Method of Preventing Cell Death Using Segment of Neural Thread Proteins," the disclosure of which is incorporated by reference herein in its entirety.

BACKGROUND OF THE INVENTION

1. Field of the Invention

The present invention relates to methods for preventing cell death, and to methods of treating conditions that require prevention, inhibition, and/or amelioration of cell death and tissue necrosis. The invention encompasses administering a segment of neural thread proteins (NTP), or a homologue, derivative, variant or mimetic thereof, to a mammal experiencing cell death. The segment can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc., either alone or conjugated to a carrier. Alternatively, the segment can be expressed in vivo by administering a gene that expresses the segment, by administering a vaccine that induces such production or by introducing cells, bacteria or viruses that express the segment in vivo, either because of genetic modification or otherwise.

2. Description of Related Art

Alzheimer's disease (AD) is a complex neurodegenerative disorder characterized by progressive impairments in memory, behavior, language, and visuo-spatial skills, ending ultimately in death. Hallmark pathologies within vulnerable regions include extracellular β-amyloid deposits, intracellular neurofibrillary tangles, synaptic loss, and extensive neuronal cell death. Research on the causes and treatments of Alzheimer's disease has led investigators down numerous avenues. Considerable evidence has implicated alterations in production or processing of the human amyloid precursor protein (APP) in the etiology of the disease. However, intensive research has proven that AD is a multifactorial disease with many different, perhaps overlapping, etiologies.

Because of this, those in the field have conducted significant research and clinical investigations to study the structural deficiencies, chemical changes, and functional abnormalities both within the brain and within different populations of nerve cells. The depth of such investigations and studies are represented by the following publications, which represent only a handful of the vast reports in this arena: *Neurobiology of Alzheimer's* Disease (D. Dawbarn and S. J. Allen, Editors), Bios, Oxford 1995; *Dementia*, (J. Whitehouse, Ed.), F. A. Davis Company, Philadelphia, 1993; *Alzheimer's Disease: Senile Dementia and Related Disorders* (Katzman, R, and R. L. Bick, Eds), Raven Press, New York, 1994, pages 47-51; *Alzheimer's Disease and Related Disorders, Etiology, Pathogenesis and Therapeutics* (Iqbol, K., et al., Eds.), Wiley, Chichester, 1999; *Alzheimer's Disease: Advances in Clinical and Basic Research* (Corain, B, Ed.), Wiley, New York, 1993; *Alzheimer's Disease: Clinical and Treatment Perspectives* (Cutler, N. R., et al., Eds.), Wiley, Chichester, 1995; *Alzheimer's Disease: Therapeutic Strategies* (Giacobini, E., Becker, R., Eds.), Birkhauser, Boston, 1994; Paykel, et al., *Arch. Gen. Psychiat.*, 51:325-332 (1994); Amaducci, et al., *Neurology*, 36:922-931 (1986); McKhann, et al., *Neurology* 34:939-944 (1984), Heston et al., *Arch. Gen. Psychiatry* 38:1085-1090 (1981); *Aging of the Brain* (Gispen and Traber, editors), Elsevier Science Publishers, Amsterdam, 1983, pages 275-282; Heyman et al., *Ann. Neurol* 15:335-341 (1984); Brayne C. and P. Calloway, Lancet 1:1265-1267 (1988); Roth et al., *Br. J. Psychiatry* 149:698-709 (1986); Medical Research Council, *Report from the NRC Alzheimer's Disease Workshop*, London, England, 1987; Morris et al., *Neurology* 41:469-478 (1991); and the references cited within each of these publications.

To date, Alzheimer's disease is the third most expensive disease in the United States, costing society approximately $100 billion each year. It is one of the most prevalent illnesses in the elderly population, and with the aging of society, will become even more significant. Costs associated with AD include direct medical costs such as nursing home care, direct non-medical costs such as in-home day care, and indirect costs such as lost patient and care giver productivity. Medical treatment and behavior modification may have economic benefits by slowing the rate of cognitive decline, delaying institutionalization, reducing care giver hours, and improving quality of life. Pharmacoeconomic evaluations have shown positive results regarding the effect of drug therapy and behavior modification on nursing home placement, cognition, and care giver time.

Neural thread proteins (NTP) are a family of recently characterized brain proteins. One member of this family, AD7C-NTP, is a ~41 kD membrane associated phosphoprotein with functions related to neuritic sprouting (de la Monte et al., *J. Clin. Invest.*, 100:3093-3104 (1997); de la Monte et al., *Alz. Rep.*, 2:327-332 (1999); de la Monte SM and Wands JR, *Journal of Alzheimer's Disease*, 3:345-353 (2001)). The gene that encodes AD7C-NTP and predicted protein sequence for AD7C-NTP has been identified and described (de la Monte et al., *J. Clin. Invest.*, 100:3093-3104 (1997)). In addition to the ~41 kD species, other species of neural thread protein (~26 kD, ~21 kD, ~17 kD, and ~15 kD) have been identified and associated with neuroectodermal tumors, astrocytomas, and glioblastomas and with injury due to hypoxia, schema, or cerebral infarction (Xu et al., *Cancer Research*, 53:3823-3829 (1993); de la Monte et al., *J. Neuropathol. Exp. Neurol.*, 55(10):1038-50 (1996), de la Monte et al., *J. Neurol. Sci.*, 138(1-2):26-35 (1996); de la Monte et al., *J. Neurol. Sci.*, 135(2):118-25 (1996); de la Monte et al., *J. Clin. Invest.*, 100:3093-3104 (1997); and de la Monte et al., *Alz. Rep.*, 2:327-332 (1999)).

Species of neural thread protein have been described and claimed in U.S. Pat. Nos. 5,948,634; 5,948,888; and 5,830,670, all for "Neural Thread Protein Gene Expression and Detection of Alzheimer's Disease" and in U.S. Pat. No. 6,071,705 for "Method of Detecting Neurological Disease or Dysfunction." The disclosures of these patents are specifically incorporated herein by reference in their entirety. As described therein, NTP is upregulated and produced during cell death. Thus, dead and dying nerve cells are described as overproducing NTP, and accordingly, its presence indicates the death of nerve cells and the onset of Alzheimer's disease (AD).

Other species of neural thread protein have been identified as other products of the AD7c-NTP gene (e.g. a 112 amino acid protein described in NCBI Entrez-Protein database Accession #XP_032307 PID g15928971) or as being similar to neural thread proteins (e.g. a 106 amino acid protein described in NCBI Entrez-Protein database Accession #AAH14951 PID g15928971, another 106 amino acid protein described in NCBI Entrez-Protein database Accession

XP_039102 PID g18599339 and a 61 amino acid protein described in NCBI Entrez-Protein database Accession #AAH02534 PID g12803421).

There is compelling evidence linking the AD7C-NTP specie of neural thread protein in particular with AD and its upregulation during cell death in AD. AD7C-NTP mRNA is upregulated in AD brain compared to controls; AD7C-NTP protein levels in brain and in CSF are higher in AD than controls; and AD7C-NTP immunoreactivity is found in senile plaques, in neurofibrillary tangles (NFT), in degenerating neurons, neuropil threads, and dystrophic neurotic sprouts in AD and Down syndrome brains (Ozturk et al., *Proc. Natl. Acad. Sci. USA*, 86:419-423 (1989); de la Monte et al., *J. Clin. Invest.*, 86(3):1004-13 (1990); de la Monte et al., *J. Neurol. Sci.*, 113(2): 152-64 (1992); de la Monte et al., *Ann. Neurol.*, 32(6):733-42 (1992); de la Monte et al., *J. Neuropathol. Exp. Neurol.*, 55(10): 1038-50 (1996), de la Monte et al., *J. Neurol. Sci.*, 138(1-2):26-35 (1996); de la Monte et al., *J. Neurol. Sci.*, 135(2):118-25 (1996); de la Monte et al., *J. Clin. Invest.*, 100:3093-3104 (1997); and de la Monte et al., *Alz. Rep.*, 2:327-332 (1999)). Immunocytochemistry demonstrated that the AD7C-NTP protein is localized within cells, within fine processes within the neuropil, or is extracellular in both AD and Down's Syndrome brains. de la Monte et al., *Ann. Neurol.*, 32(6):733-42 (1992). Two types of cells contain AD7C-NTP: neurons and astrocytes (Id.). The affected neurons are the large pyramidal type that typically contain the neurofibrillary tangles well known in AD brain (Id.).

Elevated levels of AD7C-NTP protein have been found in both CSF and urine of AD patients, showing its accuracy as a biochemical marker for this devastating illness (de la Monte and Wands, *Front Biosci* 7: 989-96 (2002); de la Monte and Wands, *Journal of Alzheimer's Disease* 3: 345-353 (2001); Munzar et al, *Alzheimer's Reports* 4: 61-65 (2001); Kahle et al, *Neurology* 54: 1498-1504 (2000) and *Averback Neurology* 55: 1068 (2000); Munzar et al, *Alzheimer Reports* 3: 155-159 (2000); de la Monte et al, *Alzheimer's Reports* 2: 327-332 (1999); Ghanbari et al, *J Clin Lab Anal* 12: 285-288 (1998); Ghanbari et al, *J Clin Lab Anal* 12: 223-226 (1998); Ghanbari et al, *Journal of Contemporary Neurology* 1998; 4A: 2-6 (1998); and de la Monte et al, *J Clin Invest* 100: 3093-3104 (1997).

Over-expression of the AD7C-NTP gene also has been linked to the process of cell death in Alzheimer's disease (de la Monte and Wands, *J. Neuropatho. and Exp. Neuro.*, 60:195-207 (2001); de la Monte and Wands, *Cell Mol Life Sci* 58: 844-49 (2001). AD7C-NTP has also been identified in Down's Syndrome brain tissue (Wands et al., International Patent Publication No. WO 90/06993; de la Monte et al, *J Neurol Sci* 135: 118-25 (1996); de la Monte et al., *Alz. Rep.*, 2:327-332 (1999)). There is some evidence that over-expression of the AD7C-NTP gene also may be associated with normal tension glaucoma (Golubnitschaja-Labudova et al, *Curr Eye Res* 21: 867-76 (2000)).

The present inventor recently discovered that released AD7C-NTP protein was cytotoxic and capable of causing cell death to other cells in tissue (as compared with up-regulated AD7C-NTP produced by the dying cell itself), as disclosed in pending U.S. patent application Ser. No. 10/092,934 and entitled "Method of Using Neural Thread Proteins to Treat Tumors and other Conditions Requiring the Removal or Destruction of Cells," the disclosure of which is incorporated by reference herein in its entirety. Accordingly, it would be desirable to prevent, inhibit, modulate or ameliorate cell death and tissue necrosis associated with neural thread proteins, especially in AD brain.

It has also recently been discovered that segments of NTP could be used in binding assays, purification of NTP, and as diagnostics as a substitute for NTP, as disclosed in pending U.S. patent application Ser. No. 09/697,590, now U.S. Pat. No. 7,259,232, and entitled: "Preferred Segments of Neural Thread Protein," the disclosure of which is incorporated by reference herein in its entirety.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to the present invention.

SUMMARY OF THE INVENTION

There exists a need to develop a method of preventing, inhibiting, modulating and/or ameliorating cell death and tissue necrosis. In particular, there exists a need to develop a method capable of preventing, inhibiting and/or ameliorating cell death and/or tissue necrosis in the brain. There also exists a need to develop a method of treating conditions associated with cell death and/or tissue necrosis. There also exists a need to develop a method of treating neurodegenerative disorders such as AD by preventing, inhibiting and/or ameliorating cell death and/or tissue necrosis in live mammalian brain tissue. There also exists a need to develop a method of controlling, inhibiting, modulating or ameliorating cell death and tissue necrosis in live tissue caused by NTP administered in order to remove or destroy harmful or unwanted tissue or cellular elements such as benign or malignant tumors in humans.

It is therefore a feature of an embodiment of the invention to provide a method of preventing, inhibiting and/or ameliorating cell death and/or tissue necrosis. The method includes contacting the live tissue with at least one segment of NTP (or a homologue, derivative, variant or mimetic thereof), whereby the segment is present in an amount sufficient to prevent, inhibit, reduce, control and/or ameliorate cell death and/or tissue necrosis.

In accordance with another feature of an embodiment of the invention, there is provided a method of preventing, inhibiting and/or ameliorating cell death and/or tissue necrosis in live mammalian brain tissue by contacting the live mammalian brain tissue with a component containing at least at least one segment of NTP (or a homologue, derivative, variant or mimetic thereof) that is present in an amount sufficient to prevent, inhibit, and/or ameliorate cell death and/or tissue necrosis. The component is capable of crossing the blood-brain barrier.

In accordance with another feature of an embodiment of the invention, there is provided a method of treating neurodegenerative disorders by contacting live mammalian brain tissue with a component containing at least one segment of NTP (or a homologue, derivative, variant or mimetic thereof). The component is capable of crossing the blood-brain barrier.

In accordance with yet another feature of an embodiment of the invention, there is provided a method of treating conditions associated with by cell death and/or tissue necrosis comprising contacting live tissue with at least one segment of NTP (or a homologue, derivative, variant or mimetic thereof). The segment of NTP is present in an amount sufficient to prevent and/or inhibit cell death and/or tissue necrosis. In accordance with this method, at least one segment of NTP (or a homologue, derivative, variant or mimetic thereof) is administered to a mammal having a condition associated with cell death and/or tissue necrosis in an amount sufficient to prevent and/or inhibit cell death and/or tissue necrosis.

In accordance with another feature of an embodiment of the invention, there is provided a composition comprising at least one segment of NTP (or a homologue, derivative, variant or mimetic thereof) and a component that enables the segment of NTP (or a homologue, derivative, variant or mimetic thereof) to cross the blood-brain barrier.

In accordance with yet another feature of an embodiment of the invention, there is provided a method of treating conditions associated with cell death and/or tissue necrosis comprising administering a gene to a mammal in need thereof, whereby the gene expresses at least one segment of NTP (or a homologue, derivative, variant or mimetic thereof), and whereby the administration results in the segment of NTP (or a homologue, derivative, variant or mimetic thereof) contacting live tissue. The gene is administered in such a fashion that the segment of NTP (or a homologue, derivative, variant or mimetic thereof) is present in an amount sufficient to prevent and/or inhibit cell death and/or tissue necrosis.

In accordance with an additional feature of an embodiment of the invention, there is provided a method of treating conditions associated with cell death and/or tissue necrosis comprising administering a vaccine to a mammal in need thereof, whereby the vaccine induces the mammal to express or otherwise produce at least one segment of NTP (or a homologue, derivative, variant or mimetic thereof), and whereby the administration results in the at least one segment of NTP (or a homologue, derivative, variant or mimetic thereof) contacting live tissue. The vaccine is administered in such a fashion that the at least one segment of NTP (or a homologue, derivative, variant or mimetic thereof) is present in an amount sufficient to prevent and/or inhibit cell death and/or tissue necrosis.

In accordance with yet another feature of an embodiment of the invention, there is provided a method of treating conditions associated with cell death and/or tissue necrosis comprising introducing or administering to or implanting in a mammal in need thereof cells, bacteria or viruses that are capable of expressing in vivo at least one segment of NTP (or a homologue, derivative, variant or mimetic thereof), whereby the cells, bacteria or viruses express at least one segment of NTP (or a homologue, derivative, variant or mimetic thereof), and whereby the administration results in at least one segment of NTP (or a homologue, derivative, variant or mimetic thereof) contacting live tissue. The cells, bacteria or viruses are introduced, administered or implanted in such a fashion and in such a quantity that at least one segment of NTP (or a homologue, derivative, variant or mimetic thereof) is present in an amount sufficient to prevent, inhibit and/or ameliorate cell death and/or tissue necrosis.

These and other features of the invention will be readily apparent to those skilled in the art upon reading the detailed description that follows. It should be understood, however, that the detailed description and the specific examples, while indicating preferred embodiments of the invention are given by way of illustration only, since various changes and modifications within the spirit and scope of the invention will become apparent to those skilled in the art from this description. Unless otherwise specified, the respective contents of the documents cited herein are hereby incorporated by reference in their entirety.

BRIEF DESCRIPTION OF THE DRAWINGS

FIG. 1 shows the complete AD7C-NTP sequence and the location of the Harlil sequences within the complete AD7C-NTP sequence (de la Monte et al., *J. Neuropathol. Exp. Neurol.*, 55:1038-1050 (1996)).

FIG. 2 shows the complete amino acid sequences (SEQ ID NO: 3) of the 122 amino acid neural thread protein (Sequence 40 from U.S. Pat. No. 5,948,634; NCBI Entrez-Protein Accession #AAE25447).

FIG. 3 shows the complete amino acid sequences (SEQ ID NO: 4) of the 112 amino acid neural thread protein (NCBI Entrez-Protein Accession #XP_032307).

FIG. 4 shows the 106 amino acid neural thread protein (SEQ ID NO: 5) listed in NCBI Entrez-Protein Accession # AAH14951 PID g15928971.

FIG. 5 shows the 106 amino acid neural thread protein (SEQ ID NO: 6) listed in NCBI Entrez-Protein Accession # XP_039102, PID g18599339.

FIG. 6 shows the complete amino acid sequences (SEQ ID NO: 7) of the 98 amino acid neural thread protein (Sequence 30 from U.S. Pat. No. 5,830,670; NCBI Entrez-Protein Accession #AAE13612).

FIG. 7 shows the complete amino acid sequences (SEQ ID NO: 8) of the 75 amino acid neural thread protein (Sequence 48 from U.S. Pat. No. 5,948,634; NCBI Entrez-Protein Accession #AAE25448).

FIG. 8 shows the complete amino acid sequences (SEQ ID NO: 9) of the 68 amino acid neural thread protein (Sequence 36 from U.S. Pat. No. 5,948,634; NCBI Entrez-Protein Accession #AAE25446).

FIG. 9 shows the complete amino acid sequences SEQ ID NO: 10) of the 61 amino acid neural thread protein-like protein (NCBI Entrez-Protein Accession #AAH02534).

DETAILED DESCRIPTION OF PREFERRED EMBODIMENTS

The term "AD7C-NTP" refers to the ~41 kD protein and the gene and the nucleic acid sequences coding for it described in de la Monte et al., *J. Clin. Invest.*, 100:3093-104 (1997), in Sequences 120 and 121 of U.S. Pat. Nos. 5,948,634, 5,948,888, and 5,830,670 and in NCBI Entrez-Protein database Accession #AF010144.

Throughout this description, the term "NTP" or "neural thread protein" refers to neural thread proteins and related molecules (including pancreatic thread protein) and the nucleic acid sequences coding for those proteins, and includes (but is not limited to) the following proteins and the nucleic acid sequences encoding the amino acid sequences for these proteins:

(a) AD7C-NTP;
(b) the ~42, ~26, ~21, ~17, ~14, and ~8 kD species of neural thread protein as described in U.S. Pat. Nos. 5,948,634, 5,948,888, 5,830,670, and 6,071,705 and in de la Monte et al., *J. Neuropathol. Exp. Neurol.*, 55(10): 1038-50 (1996), de la Monte et al., *J. Neurol. Sci.*, 138 (1-2):26-35 (1996); de la Monte et al., *J. Neurol. Sci.*, 135(2): 118-25 (1996), de la Monte et al., *J. Clin. Invest.*, 100:3093-3104 (1997) and de la Monte et al., *Alz. Rep.*, 2:327-332 (1999);
(c) proteins specifically recognized by monoclonal antibody #2 on deposit with the American Type Culture Collection, Manassas, Va., under accession number HB-12546 or monoclonal antibody #5 on deposit with the American Type Culture Collection, Manassas, Va., under accession number HB-12545;

(d) proteins coded by the AD7C-NTP gene;
(e) the 122 amino acid neural thread protein described in Sequence 40 from U.S. Pat. Nos. 5,830,670, 5,948,634, and 5,948,888 and listed in NCBI Entrez-Protein Accession #AAE25447, PID g10048540, the amino acid sequences for which is illustrated in FIG. 2;
(f) the 112 amino acid neural thread protein listed in NCBI Entrez-Protein Accession #XP_032307, PID g14725132, the amino acid sequences for which is illustrated in FIG. 3;
(g) a 106 amino acid neural thread protein-like protein listed in NCBI Entrez-Protein Accession #AAH14951 PID g15928971, the amino acid sequences for which is illustrated in FIG. 4;
(h) a 106 amino acid neural thread protein-like protein listed in NCBI Entrez-Protein Accession #XP_039102, PID g18599339, the amino acid sequences for which is illustrated in FIG. 5;
(i) the 98 amino acid neural thread protein described in Sequence 30 from U.S. Pat. Nos. 5,830,670, 5,948,634, and 5,948,888 and listed in NCBI Entrez-Protein Accession # AAE13612, PID g10048538, the amino acid sequences for which is illustrated in FIG. 6;
(j) the 75 amino acid neural thread protein described in Sequence 48 from U.S. Pat. Nos. 5,830,670, 5,948,634, and 5,948,888 and listed in NCBI Entrez-Protein Accession #AAE25448, PID g10048541, the amino acid sequences for which is illustrated in FIG. 7;
(k) the 68 amino acid neural thread protein described in Sequence 36 from U.S. Pat. Nos. 5,830,670, 5,948,634, and 5,948,888 and listed in NCBI Entrez-Protein Accession #AAE25446, PID g10048539, the amino acid sequences for which is illustrated in FIG. 8;
(l) the 61 amino acid neural thread protein-like protein listed in NCBI Entrez-Protein Accession #AAH02534, PID g12803421, the amino acid sequences for which is illustrated in FIG. 9;
(m) pancreatic thread protein;
(n) the neural pancreatic thread protein (nPTP) described in U.S. Pat. No. 6,071,705; and
(o) proteins specifically recognized by the antibodies produced by a hybridoma from the group consisting of HB 9934, HB 9935, and HB 9936 deposited at the American Type Culture Collection.

The term "NTP" also includes NTP derived from mammalian tissue or produced using recombinant techniques and includes fragments, variants, derivatives, and homologues of NTP.

Amino acids and amino acid residues described herein may be referred to according to the accepted one or three-letter code provided in the table below. Unless otherwise specified, these amino acids or residues are of the naturally occurring L stereoisomer form.

TABLE 1

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, the term or "Harlil sequence" or "Harlil peptide" refers to a biologically active peptide that comprises or contains one or more of the following sequences:
1. T H A R L I L (SEQ ID NO: 22): H H A R L C L (SEQ ID NO: 19): M F A R L I L (SEQ ID NO: 27): and H H A R L I F (SEQ ID NO: 21): as described in FIG. 1;
2. H H A R L (SEQ ID NO: 15): H A R L (SEQ ID NO: 16): H A R L I (SEQ ID NO: 17): H A R L I L (SEQ ID NO: 18): H H A R L C L (SEQ ID NO: 19): A R L I L (SEQ ID NO: 20): H H A R L I F (SEQ ID NO: 21): T H A R L I L (SEQ ID NO: 22): A R L I (SEQ ID NO: 23): A R L: H A R L C L (SEQ ID NO: 24): A R L C L (SEQ ID NO: 25): A R C L (SEQ ID NO: 26): M F A R L I L (SEQ ID NO: 27): F A R L I L (SEQ ID NO: 28): F A R L I (SEQ ID NO: 29): F A R L (SEQ ID NO: 30): H A R L I F (SEQ ID NO: 31): and A R L I F (SEQ ID NO: 32):
3. L H A R L C L A N F C G R N R V ("NTP-1") (SEQ ID NO: 33):
4. L A R L C L A N F C G N N N V ("NTP-2") (SEQ ID NO: 34):
5. C A R Y R T G H H A R L M ("NTP-3") (SEQ ID NO: 35):
6. H H A R L P L A N F C G ("NTP-4") (SEQ ID NO: 36):
7. R T G H H A R L C L A N F C ("NTP-5") (SEQ ID NO: 37):
8. C E S A R Y R T G H H A R L C ("NTP-6") (SEQ ID NO: 38):
9. D N T H H A R L I L ("NTP-7") (SEQ ID NO: 39):
10. S H H A R L I L ("NTP-8") (SEQ ID NO: 40): and
11. H A R L M L (SEQ ID NO: 41): H A R L V L (SEQ ID NO: 42): and H A K L I L (SEQ ID NO: 43)

The term "Harlil sequence" or "Harlil peptide" as it is used herein also includes biologically active variants, homologues, derivatives and peptide mimetics of Harlil sequences or Harlil peptides and includes biologically active peptides containing the sequence of any of the sequences listed in subparagraphs 1 to 11 above with additional amino acid residues before or after the Harlil sequence on linker peptides.

As used herein, the term "segment of NTP" refers to a biologically active fragment of a species of NTP, preferably AD7C-NTP, and specifically includes (but is not limited to) Harlil sequences and Harlil peptides.

The term "biologically active" refers to a protein, peptide, Harlil peptide, or segment of NTP that has the ability of binding to NTP or other molecules.

The term "fragment" refers to a protein or polypeptide that consists of a continuous subsequence of the amino acid sequence of a NTP protein or segment of NTP and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same NTP protein or segment of NTP, with a contiguous amino acid sequence in common or not, joined together, either directly or through a linker.

The term "variant" refers to a protein or polypeptide in which one or more amino acid substitutions, deletions, and/or insertions are present as compared to the amino acid sequence of an NTP protein or segment of NTP and includes naturally occurring allelic variants or alternative splice variants of an NTP protein or segment of NTP. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, *Sequence Analysis in Molecular Biology*, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

Conservative Amino Acid Substitutions

| Basic: | arginine |
| --- | --- |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

Table 3 sets out another scheme of amino acid substitution:

TABLE 3

| Original Residue | Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |

TABLE 3-continued

| Original Residue | Substitutions |
| --- | --- |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include NTP proteins or segments of NTP with additional amino acid residues before or after the NTP or segment of NTP amino acid sequence on linker peptides. For example, a cysteine residue may be added at both the amino and carboxy terminals of a segment of NTP in order to allow the cyclisation of the segment of NTP by the formation of a di-sulphide bond. The term "variant" also encompasses polypeptides that have the amino acid sequence of a Harlil peptide with at least one and up to 25 additional amino acids flanking either the 3' or 5' end of the Harlil peptide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type NTP proteins or segments. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *Proteins—Structure And Molecular Properties,* 2nd Ed., T. E. Creighton, W. H. Freeman and Company, New York (1993) and Wold, F., "Posttranslational Protein Modifications: Perspectives and Prospects," pgs. 1-12 in *Posttranslational Covalent Modification Of Proteins,* B. C. Johnson, Ed., Academic Press, New York (1983); Seifter et al., *Meth. Enzymol.* 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 75 percent identical in its amino acid sequence of an NTP protein, AD7C-NTP or a segment of NTP, as the case may be, as determined by standard methods that are commonly used to compare the similarity in position of the amino acids of two polypeptides. The degree of similarity or identity between two proteins can be readily calculated by known methods, including but not limited to those described in *Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part I,* Griffin, A. M., and Griffin, H. G., eds., Humana Press, New Jersey, 1994; *Sequence Analysis in Molecular Biology,* von Heinje, G., Academic Press, 1987; *Sequence Analysis Primer,* Gribskov, M. and Devereux, J., eds., M Stockton Press, New York, 1991; and Carillo H. and Lipman, D., SIAM, *J. Applied Math.,* 48: 1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., *Nucleic Acids Research,* 12(1): 387 (1984)), BLASTP, BLASTN, and FASTA, Atschul, S. F. et al., *J. Molec. Biol.,* 215: 403-410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.,* 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3× (times) the average diagonal; the "average diagonal" is the average of the diagonal of the comparison matrix being used; the "diagonal" is the score or number assigned to each perfect amino acid by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al. in: *Atlas of Protein Sequence and Structure,* vol. 5, supp.3 [1978] for the PAM250 comparison matrix; see Henikoff et al., *Proc. Natl. Acad. Sci USA,* 89:10915-10919 [1992] for the BLOSUM 62 comparison matrix) also may be used by the algorithm. The percent identity then is calculated by the algorithm. Homologues will typically have one or more amino acid substitutions, deletions, and/or insertions as compared with NTP, AD7c-NTP, a segment of NTP, or Harlil sequence.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to this invention provide a spatial arrangement of reactive chemical moieties that closely resemble the three-dimensional arrangement of active groups in the antibody, antibody derivative or antibody fragment on which the peptide mimetic is based. As a result of this similar active-site geometry, the peptide mimetic has effects on biological systems that are similar to the biological activity of the peptide.

The peptide mimetics of this invention are preferably substantially similar in both three-dimensional shape and biological activity to the segments of NTP described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala$^1$-Peptide T Binding", Smith C. S. et al., *Drug Development Res.,* 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the segment of NTP by pseudopeptide bonds that confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", *Escom, Leiden* (1990), pp. 722-773) and Dalpozzo, et al. (1993), *Int. J. Peptide Protein Res.,* 41:561-566, incorporated herein by reference). According to this modification, the amino acid sequences of the peptides may be identical to the sequences of a segment of NTP described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond is a (Couder, et al. (1993), *Int. J. Peptide Protein Res.*, 41:181-184, incorporated herein by reference in its entirety).

Thus, the amino acid sequences of these peptides may be identical to the sequences of a segment of NTP or Harlil sequence, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of segments of NTP or Harlil sequence represent another class of peptide mimetics that retain the important structural determinants for biological activity, yet eliminate the peptide bonds, thereby conferring resistance to proteolysis (Simon, et al., 1992, *Proc. Natl. Acad. Sci. USA*, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the segment of NTP or Harlil sequence may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of a segment of NTP or Harlil sequence. Thus, the carboxy terminal residue of an L-amino acid segment of NTP becomes the amino terminal for the D-amino acid peptide and so forth. For example, the AD7c-NTP fragment, HARLIL, becomes $L_d I_d L_d R_d A_d H_d$, where $A_d$, $H_d$, $I_d$, $L_d$, and $R_d$ are the D-amino acids corresponding to the L-amino acids, A, H, I, L, and R respectively.

The term "enantiomer" refers to a biologically active protein or peptide where one or more the L-amino acid residues in the amino acid sequence of a segment of NTP is replaced with the corresponding D-amino acid residue(s).

Throughout this description, the term "neurodegenerative disorder" refers to:

1. pathological conditions characterized by one or more of the following signs: brain atrophy, cell loss, neurofibrillary tangles, amyloid plaques, and/or the presence of NTP in tissue and/or bodily fluids;
2. the Alzheimer group of diseases, namely, Alzheimer's disease (pre-senile dementia, senile dementia); Alzheimer's disease associated with Down's syndrome; familial Alzheimer's Disease; genetic Alzheimer's disease due to mutations such as Presenilin 1, Presenilin 2, and others; Alzheimer's disease associated with other central-nervous-system diseases, such as Parkinson's disease, Lewy Body Disease, and cerebrovascular diseases;
3. congophilic angiopathy (associated or not associated with Alzheimer's disease, familial or not familial);
4. pathological conditions characterized by the deposition of abnormal fibrils ("amyloid fibrils") and/or related non-fibrillar amyloid precursor or non-precursor molecule(s);
5. pathological conditions characterized by the abnormal deposition of tau including frontotemporal dementia, progressive supranuclear palsy (PSP), corticobasal ganglionic degeneration (CBD) and conditions relating to mutations of the tau gene; and/or
6. other disorders and diseases such as those disclosed in U.S. Pat. No. 6,001,331, the disclosure of which is incorporated by reference herein in its entirety.

Throughout this description, the expressions "amyloid plaques" and "amyloid fibrils" denote senile plaques, neuritic plaques, amyloid plaques, amyloid stars, amyloid cores, primitive plaques, classical plaques, burn out plaques, diffuse plaques, shadow plaques, neurofibrillary tangles, amyloid fibrils, paired helical filaments, and the like.

Throughout this description, the term "mammal" denotes all mammals, and preferably denotes, sheep, cows, dogs, cats, apes, monkeys, mice, rats, and humans, and most preferably denotes a human.

Throughout this description, the expressions "segment of NTP," "Harlil sequence" and "Harlil peptide" are used interchangeably. It is to be understood that, whenever "segment of NTP," "Harlil sequence" or "Harlil peptide" is used, the invention encompasses suitable homologues, variants, derivatives and peptic mimetics thereof.

Throughout this description, the expression "tissue containing NTP" denotes tissue containing all or a portion of NTP, tissue in cellular communication with NTP that may or may not otherwise contain it, tissue that has been contacted with NTP, but no longer contains it in its original form, and tissue that may at some point in time be in contact with NTP.

The present invention is directed toward methods of preventing cell death and/or tissue necrosis. While NTP has been known and described in the literature, it was not heretofore known that NTP was a cause of cell death of cells other than the cells producing the NTP. While not intending on being bound by any theory, the present inventor believes that the presence of NTP in live tissue not only is an indication of certain nerve cell death, as previously reported, but it also is toxic insofar as it causes other live tissue cell death. The present inventor believes that AD7C-NTP in particular present in live mammalian brain tissue is a marker for Alzheimer's Disease (AD), and it exacerbates AD by causing cell death and/or tissue necrosis in the live tissue in which it exists.

Accordingly, it is believed that, as a mammal becomes inflicted with AD, nerve cell death up-regulates the gene that preferably produces AD7C-NTP, thereby producing AD7C-NTP at that site. The AD7C-NTP so produced then begins destroying other live tissue (e.g., other nerve cells, glial cells, etc.) in the vicinity thereof, thereby exacerbating the progression of the disease. The inventor therefore believes that neutralizing the effect of, for example, AD7C-NTP will help prevent, inhibit, and/or ameliorate cell death and/or tissue necrosis in live tissue that contains, for example, AD7C-NTP. It was surprising to find that segments of NTP could bind to the AD7C-NTP and prevent, inhibit, and/or ameliorate cell death and/or tissue necrosis in live tissue that contains AD7C-NTP.

NTP is known and described in, for example, U.S. Pat. Nos. 5,948,634, 5,948,888, 5,830,670, and 6,071,705, the disclosures of which are incorporated by reference herein in their entirety. Methods of making NTP recombinantly or otherwise are disclosed in the aforementioned documents. Raising antibodies against NTP so that one can diagnose AD and other associated disorders and diseases, also is disclosed in these documents. It will be evident to those skilled in the art that one may use NTP homologues, derivatives, mimetics and variants, as well as NTP from diverse sources (e.g., natural, pancreatic, purified, synthesized, or from different expression systems in vitro, etc.) to make any of the segments useful in the present invention.

The present invention is directed to a method of preventing and/or inhibiting cell death and/or tissue necrosis. The method includes contacting live tissue with at least one segment of NTP, whereby the segment is present in an amount sufficient to prevent and/or inhibit cell death and/or tissue necrosis. The segment of NTP preferably is a subsequence of AD7C-NTP and most preferably contains at least one of the following repeat sequences of AD7C-NTP:

| (a) | 45–51 | T H A R L I L (SEQ ID NO: 22) |
|---|---|---|
| (b) | 90–96 | H H A R L C L (SEQ ID NO: 19) |
| (c) | 263–269 | M F A R L I L (SEQ ID NO: 27) |
| (d) | 291–297 | H H A R L I F (SEQ ID NO: 21) |

See FIG. 1.

The invention encompasses peptides having the sequence of any of regions (a), (b), (c), (d), or homologues, derivatives, variants and mimetics of these (including but not limited to "H A R L M L" (SEQ ID NO: 41). The Harlil peptides also can have additional amino acid residues before or after the Harlil sequence on linker peptides. The additional amino acid residues or linker peptides may be those found in the NTP sequence before and after the Harlil sequence. For example, the amino acid residues G I T G M C T (SEQ ID NO: 11) occur before residue 46 and the amino acid residues Y F F L V (SEQ ID NO: 13) occur after amino acid 51 in the NTP sequence. Thus, a Harlil peptide useful as a segment of NTP in the present invention can include the NTP peptide G I T G M C T H A R L I L Y F F L V (SEQ ID NO: 12). For the Harlil peptides recited in (b), (c), and (d), the additional amino acid residues preferably are those that flank the Harlil sequence in the NTP sequence. Preferably, the Harlil peptide having additional amino acid residues does not exceed 25 total amino acid residues in length.

The Harlil repeat sequence preferably has the unique characteristic of binding to NTP. This ability to bind to NTP suggests that the Harlil repeat sequence is useful in preventing, inhibiting or ameliorating cell death and/or tissue necrosis in live tissue containing NTP.

The present invention is directed to the use of Harlil sequence peptides and their homologues, derivatives, variants and peptide mimetics as affinity binding partners of NTP and other molecules for the treatment of conditions associated with cell death and/or tissue necrosis. The invention also is directed to methods of treating conditions associated with cell death and/or tissue necrosis as well as compositions containing Harlil peptides or their homologues, derivatives, variants, and peptide mimetics that are capable of crossing the bbb.

Harlil peptides and homologues, derivatives, and variants thereof can be made using conventional peptide synthesis techniques. Mimetics of Harlil peptides can be developed using combinatorial chemistry techniques.

Nucleic acids corresponding to Harlil peptides can be made, for example, using (a) standard recombinant methods, (b) synthetic techniques, or (c) combinations thereof.

Harlil sequences bind to AD7C-NTP and other molecules. See pending U.S. patent application Ser. No. 09/697,590, now U.S. Pat. No 7,259,232, and entitled: "Preferred Segments of Neural Thread Protein," the disclosure of which is incorporated by reference herein in its entirety.

This invention includes the surprising discovery that a Harlil sequence that can bind to AD7C-NTP can prevent or inhibit cell death and/or tissue necrosis in live tissue containing AD7C-NTP.

There is evidence that AD7C-NTP participates in the neurodegenerative cascade. The ability to interrupt or redirect the cascade by targeting AD7C-NTP offers a therapeutic opportunity. For example, it may be possible to intervene therapeutically by using the ability of the Harlil peptides to interact with AD7C-NTP binding sites, thus blocking potential reactive sites on AD7C-NTP.

Alternatively, the Harlil peptides of the invention may be useful to target drugs to cells expressing the Harlil sequence, or to create genes or vaccines that induce expression of the Harlil sequence in vivo.

Although the actual mechanism by which the Harlil sequence operates is not yet known, the present inventor has found that administration of a Harlil sequence to live tissue that contains AD7C-NTP prevents and/or inhibits and/or ameliorates cell death and tissue necrosis that otherwise occurs in the absence of the Harlil sequence.

It is possible that the "HARLIL" sites interact with other brain proteins and may play a role in the functionality of AD7C-NTP and/or other NTP or other molecules.

Methods of making and detecting such Harlil sequences, or their functional homologues or analogues are described in copending United States patent application Ser. No. 09/697, 590, now U.S. Pat No. 7,259,232, and entitled: "Preferred Segments of Neural Thread Protein," the disclosure of which is incorporated by reference herein in its entirety.

The peptide segments of NTP that are particularly useful in the context of the present invention are those described above that include at least a portion of the HARLIL (SEQ ID NO: 18) amino acid sequence of AD7C-NTP. Useful Harlil sequences include those amino acid sequences selected from the following list:

(a) H H A R L (SEQ ID NO: 15):
(b) H A R L (SEQ ID NO: 16):
(c) H A R L I (SEQ ID NO: 17):
(d) H A R L I L (SEQ ID NO: 18):
(e) H H A R L C L (SEQ ID NO: 19):
(f) A R L I L (SEQ ID NO: 20):
(g) H H A R L I F (SEQ ID NO: 21):
(h) T H A R L I L (SEQ ID NO: 11):
(i) A R L I (SEQ ID NO: 23):
(j) A R L:
(k) H A R L C L (SEQ ID NO: 24):
(l) A R L C L (SEQ ID NO: 25):
(m) A R C L (SEQ ID NO: 26):
(n) M F A R L I L (SEQ ID NO: 27):
(O) F A R L I L (SEQ ID NO: 28):
(p) F A R L I (SEQ ID NO: 29):
(q) F A R L (SEQ ID NO: 30):
(r) H A R L I F (SEQ ID NO: 31):
(s) A R L I F (SEQ ID NO: 32):

and homologues, variants, derivatives and mimetics thereof.

Various peptides selected from the above list, and homologues, variants, derivatives and mimetics thereof can be used in the present invention as the segment of NTP. For example, the peptide can have the amino acid sequence A R L I (SEQ ID NO: 23), and comprise at least one and up to 25 additional amino acids flanking either the 3' or 5' end of the peptide. The peptide also can have the amino acid sequence H A R L (SEQ ID NO: 16), and comprise at least one and up to 25 additional amino acids flanking either the 3' or 5' end of the peptide. In addition, the peptide can have the amino acid sequence F A R L (SEQ ID NO: 30), and comprise at least one and up to 25 additional amino acids flanking either the 3' or 5' end of the peptide. The peptide also can be selected from one that has the amino acid sequence A R L, and comprising at least one and up to 25 additional amino acids flanking either the 3' or 5' end of the peptide. Yet another useful peptide in the present invention includes those having the amino acid sequence A R L C (SEQ ID NO: 14), and comprising at least one and up to 25 additional amino acids flanking either the 3' or 5' end of the peptide. Finally, the segment of NTP can be a polymer of a Harlil peptide sequence comprising at least two repetitions of the peptide.

It is even more preferred in the present invention that the Harlil sequences be peptides having the following amino acid sequences.

| 1. | (NTP-1) | L H A R L C L A N F C G R N R V (SEQ ID NO: 33) |
|---|---|---|
| 2. | (NTP-2) | L A R L C L A N F C G N N N V (SEQ ID NO: 34) |
| 3. | (NTP-3) | C A R Y R T G H H A R L M (SEQ ID NO: 35) |
| 4. | (NTP-4) | H H A R L P L A N F C G (SEQ ID NO: 36) |
| 5. | (NTP-5) | R T G H H A R L C L A N F C (SEQ ID NO: 37) |
| 6. | (NTP-6) | C E S A R Y R T G H H A R L C (SEQ ID NO: 38) |
| 7. | (NTP-7) | D N T H H A R L I L (SEQ ID NO: 39) |
| 8. | (NTP-8) | S H H A R L I L (SEQ ID NO: 40) |

The above sequences can be conjugated to carrier proteins through a cysteine. Thus, peptides NTP-1 and NTP-2 produced mixed conjugate results due to the presence of more than one cysteine residue. Therefore, for peptides NTP-5 and NTP-6, the secondary cysteine was blocked with Acetamido Methyl ($C_3H_6NO$) (ACM).

The location of the identified sequences in the AD7C-NTP can be seen from FIG. 1. While all of the Harlil analogues showed some reactivity, particularly preferred Harlil analogs are those selected from NTP-1, NTP-3, and NTP-7. It should be noted that in the Harlil analog NTP-1, the first amino acid, "L" may be replaced with Lysine, or "K."

The Harlil sequences, or segments of NTP preferably are contacted with live tissue containing NTP. Any live tissue that contains NTP, that was contacted by NTP and the NTP no longer exists or does not exist in its original form, or that might at some point in time contain NTP is encompassed by the present invention. Preferably, the tissue is tissue selected from mammalian tissue.

An embodiment of the invention includes a method of treating conditions caused by necrosis of live tissue containing NTP. In this context, the necrosis of live tissue and cell death denotes cell death and/or tissue necrosis of cells other than the dying cells that produce the NTP. In the method, a segment of NTP or a Harlil sequence is administered to a mammal suffering from such a condition. The Harlil sequence is administered in an amount and for a period of time sufficient to prevent and/or inhibit the live tissue necrosis.

Those skilled in the art will appreciate that instead of directly administering the Harlil sequence, the Harlil sequence or homologue, variant, derivative or mimetic thereof, can be produced or expressed by the mammal through gene expression (e.g., gene therapy) or through a vaccine. Skilled artisans are capable of creating, isolating and purifying suitable genes or vaccines useful in inducing expression of a Harlil sequence, or homologues, derivatives, variants or mimetics thereof, using the guidelines provided herein.

For example, gene therapy has attracted wide attention as a method to treat various mammalian diseases and enhance production of specific proteins or other cellular products. Gene therapy generally is accomplished by introducing exogenous genetic material into a mammalian patient's cells. The introduced genetic material can be designed to replace an abnormal (defective) gene of the mammalian patient ("gene replacement therapy"), or can be designed for expression of the encoded protein or other therapeutic product without replacement of any defective gene ("gene augmentation"). Because many congenital and acquired medical disorders result from inadequate production of various gene products, gene therapy provides a means to treat these diseases through either transient or stable expression of exogenous nucleic acid encoding the therapeutic product.

Gene therapy can be accomplished by either direct transformation of target cells within the mammalian subject (in vivo gene therapy) or transformation of cells in vitro and subsequent implantation of the transformed cells into the mammalian subject (ex vivo gene therapy). In vivo gene therapy is particularly preferred for use in the present invention. In addition to repair of somatic cells, it is generally known that in vivo gene therapy also can be used for systemic treatment, an area in which gene therapy has broad applications. Systemic treatment involves transfecting target cells with the DNA of interest, expressing the coded protein in that cell, and the capability of the transformed cell to subsequently secrete the manufactured protein into blood.

A variety of methods have been developed to accomplish in vivo transformation including mechanical means (e.g, direct injection of nucleic acid into target cells or particle bombardment), recombinant viruses, liposomes, and receptor-mediated endocytosis (RME) (for reviews, see Chang et al. 1994 *Gastroenterol.* 106:1076-84; Morsy et al. 1993 *JAMA* 270: 2338-45; and Ledley 1992 *J. Pediatr. Gastroenterol. Nutr.* 14:328-37).

Suitable methods of developing and administering genes and vaccines suitable to induce in vivo expression of the Harlil sequences or segments of NTP, or homologues, variants, derivatives or mimetics thereof are disclosed in, for example, U.S. Pat. Nos. 6,210,919 and 6,225,290. The disclosures of each of these patents are incorporated by reference herein in their entirety.

Any condition associated with cell death and necrosis can be treated in accordance with the present invention. Preferably, the condition is selected from a neurodegenerative disease such as AD, Pick's Disease, Lewy body Disease, or Parkinson's Disease, or from stroke, brain tumor, and other brain diseases, or glaucoma.

In accordance with preferred embodiments of the invention, the method includes contacting live tissue with at least one segment of NTP (or homologue, derivative, variant or mimetic thereof) in an amount sufficient to prevent cell death and/or tissue necrosis. Methods of administering the segment of NTP include administering the segment of NTP intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc., either alone or conjugated to a carrier. In addition, the segment of NTP can be expressed or produced in vivo by administration of a gene that expresses the protein, by administration of a vaccine that induces such production, or by introduction of cells, bacteria or viruses that express the segment in vivo, as described above.

The treatment of nervous system disorders or other brain-related disorders can be achieved by administering drugs that affect nervous system function or dysfunction in animals or patients. Typically, such drugs are administered by peripheral application, either via the oral or the systemic route. While some drugs are able to cross the blood brain barrier (bbb), others do not pass the bbb efficiently or not at all and are only effective when given directly into the brain. The term "blood-brain barrier" or "bbb", as used herein, refers to the bbb proper as well as to the blood-spinal barrier. The blood-brain barrier, which consists of the endothelium of the brain vessels, the basal membrane and neuroglial cells, acts to limit penetration of substances into the brain. Sometimes the structure of the bbb is subdivided into two components: the endothelial or capillary barrier and the ependymal barrier. Banks, W. A., Kastin, A. J., Barrera, "Delivering peptides to the central nervous system: Dilemmas and strategies," *Pharm. Res.* 8:1345-1350 (1991).

The nature of the substance penetration through the bbb has not yet been determined but it is known that many of the regulators of brain function such as cytokines, transferrin, encephalins and endorphines can pass through the bbb from the blood vessels into the brain Raeissi, S., Audus, J., "In vitro characterization of blood-brain barrier permeability to delta sleep-inducing peptide." *J. Pharm. Phy.* 41:848-852 (1989); Zlokovich, B., Susie, V. T., Davson, H. Begley, D. J., Jankov, R. M., Mitrivic, B. M., Lipovac, M. N., "Saturable mechanism for delta sleep-inducing peptide (DSIP) at the blood-brain barrier of the vascularly perfused guinea pig brain." *Peptides* 10:249-254(1989); and Zlokovich, B., "In vivo approaches for studying peptide interaction at the blood-brain barrier." *J. Control. Rel.* 13:185-201(1990). However, many substances that can affect the Central Nervous System (or CNS) such as adenosine, β-endorphin, synthetic analogs of endogenous peptides Houghten, R. A. Swann, R. W., Li, C. H., "β-Endorphin: Stability, clearance behaviour and entry into the central nervous system after intravenous injection of the tritiated peptide in rats and rabbits." *Proc. Natl. Acad. Sci. USA* 77:4588-4591(1980); Levin, E. R., Frank, H. J. K., Weber, M. A., Ismail, M., Mills M., "Studies on penetration of the blood-brain barrier by atrial natriuretic factor." *Biochem. Biophys. Res. Commun.* 147:1226-1231(1987) Sakane, T., Tanaka, C., Yamamoto, A., Hashida, M., Sesaki, H., Ueda, H., Takagi, H., "The effect of polysorbate 80 on brain uptake and analgesic effect of D-kyoto." *Int. J. Pharm.* 57:77-83(1989), as well as some excitatory and inhibitor amino acids and trophic factors, penetrate poorly or not at all through the bbb. At present, drugs with no bbb penetration or poor bbb penetration can only be given by direct CNS infusion or by implantation of controlled-release polymers. (See, e.g., U.S. Pat. No. 4,883,666, Sabel et al.).

One way to overcome some of the limitations of traditional drug therapy is to increase the relative amount of drug that passes the bbb. The belief is that if one can increase the amount of the drug crossing the bbb while reducing the peripheral dose of a given drug or diagnostic substance, the peripheral side effects of the drug are also less severe, while at the same time maintaining the desired effect in the brain. A number of approaches have been described as effective in increasing drug penetration through the bbb.

One approach has been to alter the function of the bbb itself. For instance, osmotic agents, when given peripherally (such as by intravenous injection), result in the opening of the bbb. Further, some drugs acting on the CNS can change the permeability of the bbb for other substances; cholinomimetic arecolines, for instance, have been reported to induce changes of drug penetration through the bbb Saija, A., Princi, P., De Pasquale, R., Costa, G., "Arecoline but not haloperidol produces changes in the permeability of the blood-brain barrier in the rat." *J. Pharm. Pha.* 42:135-138 (1990).

Other drugs that can be administered to alter the permeability of the bbb are disclosed in U.S. Pat. Nos. 5,059,415 and 5,124,146, both issued to E. A. Neuwelt. Bradykinin is one specific drug with such effects. (U.S. Pat. No. 5,112,596, issued to Malfroy-Camine). Another method comprises administering permeabilizer peptides such as A-7 or conformational analogs thereof. (WO 92/18529, an application of J. W. Kozarich et al.). A relatively invasive method has been proposed by A. Tomasz and E. Tuomanen (WO 91/16064) who administer parenteral injections of purified cell wall or cell wall fragments of eubacteria such as *Streptococcus pneumoniae* to open the bbb.

U.S. Pat. No. 5,260,210 issued to L. L. Rubin et al., discloses a method whereby the permeability of the blood-brain barrier is increased by administering an agent that reduces or interferes with cyclic AMP concentrations or that increases cyclic GMP concentrations.

Another approach is the modification of the drug molecules themselves. For instance, macromolecules, such as proteins, do not pass the bbb at all, or pass through with difficulty or with alterations that adversely impact the proteins efficacy. For example, one can first isolate the macromolecule active site, i.e., the portion of the molecule that triggers the biologically desirable event, and then use only this active site. Since size is one of the factors in allowing permeability of the bbb, the reduced size can be used so that the smaller molecule can now pass the bbb. Other modifications to macromolecules to attempt passage of the bbb include glycating the proteins, thereby enhancing their permeability of the bbb, or forming a prodrug. U.S. Pat. No. 5,260,308, issued to J. F. Podusio and G. L. Curran, discusses glycating proteins, while U.S. Pat. No. 4,933,324 and WO 89/07938, both on applications of V. E. Shashoua, disclose formation of a prodrug. These prodrugs are formed from a fatty acid carrier and a neuroactive drug which is unable to pass across the bbb on its own. A similar system is disclosed in WO 89/07938.

Still another approach is the implantation of controlled release polymers that release the active ingredient from a matrix-system directly into the nervous tissue. However, this approach is invasive and requires surgical intervention if implanted directly into the brain or spinal cord (see Sabel et al. U.S. Pat. No. 4,883,666; and Sabel et al. U.S. patent application Ser. No. 07/407,930). It also is known to administer compositions directly to internal portions of the brain, as disclosed on U.S. Pat. No. 5,800,390, the disclosure of which is incorporated by reference herein in its entirety. These methods enable the delivery of sustained release, solid preparations and semi-solid preparations directly to brain tissue.

To overcome these limitations, another approach has been tried in which drug carrier systems are used such as liposomes, erythrocyte ghosts, antibody-conjugates, and monoclonal antibody conjugates. One of the major problems in targeted drug delivery is the rapid opsonization and uptake of injected carriers by the reticuloendothelial system (RES), especially by the macrophages in the liver and spleen. This obstacle may be partially overcome in the case of liposomes by incorporation of so-called "stealth" lipids, such as phosphatidylinositol, monosialoganglioside, or sulfogalactosylceramide.

U.S. Pat. Nos. 5,182,107 and 5,154,924, both issued to P. M. Friden, teach a method of conjugating a drug with an antibody where the antibody is reactive with a transferrin receptor. Transferrin receptors are located on brain capillary endothelial cells, which thus can transport a drug, such as nerve growth factor, across the bbb. U.S. Pat. No. 5,004,697 (issued to Pardridge) improves such an antibody-conjugate method by providing cationized antibodies with a specific isoelectric point (see also WO 89/01343 by Pardridge).

Another approach is to create chimeric peptides to which the active agents are conjugated (U.S. Pat. No. 4,801,575, also issued to Pardridge). Such a system is further discussed also in U.S. Pat. No. 4,902,505, issued to Pardridge and Schimmel, in which the chimeric peptide, such as histone, is capable of crossing the bbb by transcytosis.

U.S. Pat. Nos. 5,187,158 and 5,017,566, both issued to N. S. Bodor, disclose a brain-specific drug delivery method wherein a centrally acting drug is given with the reduced, biooxidizable lipoidal form of a dihydropyridine reaction-pyridine salt redox carrier such as dopamine. (See also U.S. Pat. No. 4,880,816, also issued to Bodor).

A rather invasive approach is taken to deliver genetic material to the brain. This is done, for example, by chemically disrupting the bbb and then using viruses to deliver genes across the bbb. (See, U.S. Pat. No. 4,866,042, issued to E. A. Neuwelt). Here, a corrective genetic material is incorporated into a virus and the virus is then injected into the bloodstream.

Finally, yet another carrier system to deliver drugs across the bbb is the use of liposomes, as disclosed by F. D. Collins and R. C. Thompson (WO 91/04014). Here, liposomes are targeted to specific endogenous brain transport systems that transport specific ligands across the bbb.

Another approach is disclosed in U.S. Pat. No. 6,117,454, to Kreuter, et al. The subject matter of the Kreuter patent includes a method, composition and drug targeting system using surfactant coated nanoparticles as a drug carrier (or targeting molecule) for a wide range of drugs in order to enhance the penetration of drugs or diagnostic agents across the bbb.

Another approach is to administer the drugs intranasally, allowing for direct access to the brain and bypassing the bloodstream. This has been successfully done in an experimental model for three neuropeptides, melanocortin, vasopressin and insulin: Born J et al. "Sniffing neuropeptides: a transnasal approach to the human brain" *Nature Neuroscience Advance* online publication: May 6, 2002, DOI: 10.1038/nn849.

Solid dosage forms for oral administration include capsules, tablets, pills, powders, and granules. In such solid dosage forms, the active compound usually is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (O) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active Harlil sequence compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like. Besides such inert diluents, the composition can also include adjuvants, such as wetting agents, emulsifying and suspending agents, sweetening, flavoring, and perfuming agents.

Another method of administering the segment of NTP is by a transdermal or transcutaneous route. One example of such an embodiment is the use of a patch. In particular, a patch can be prepared with a fine suspension of segment of NTP in, for example, dimethylsulfoxide (DMSO), or a mixture of DMSO with cottonseed oil and brought into contact with the skin of the mammals away from the treatment site. The composition may be present inside a skin pouch. Other mediums or mixtures thereof with other solvents and solid supports would work equally as well. The patch can contain the segment of NTP in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

Actual dosage levels of the active ingredients in the compositions of the invention may be varied to obtain a segment to NTP-containing composition that is effective in obtaining a desired tissue necrosis-inhibiting therapeutic response for a particular composition and method of administration. The selected dosage level therefore depends upon the desired therapeutic effect, the route of administration, the desired duration of treatment, and other factors.

With mammals, including humans, the effective amounts can be administered on the basis of body surface area. The interrelationship of dosages for animals of various sizes, species, and humans (based on $mg/M^2$ of body surface) is described by E. J. Freireich et al., *Cancer Chemother. Rep.*, 50(4):219 (1966). Body surface area may be approximately determined from the height and weight of an individual (see e.g., Scientific Tables, Geigy Pharmaceuticals, Ardsley, N.Y. pp. 537-538 (1970)).

The total daily dose of the segment of NTP that is administered to a host may be in single or divided doses. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

The segment of NTP-containing compositions of the present invention preferably contain a component that enables the segment of NTP to cross the blood-brain barrier to treat live brain tissue. Any of the variety of components described above can be used to render the segments capable of crossing the blood-brain barrier. For example, the segments of NTP may be small enough to traverse the blood-brain barrier. In this case, no additional component would be required.

The segments of NTP thereof may be glycated to enhance the permeability of the bbb, as disclosed in U.S. Pat. No. 5,260,308, or formed into a prodrug, as disclosed in U.S. Pat. No. 4,933,324 and WO 89/07938. These prodrugs preferably are formed from a fatty acid carrier and an segment of NTP, which is unable to pass across the bbb on its own.

An alternative approach is the implantation of controlled release polymers that release the segments of NTP from a matrix-system directly into the nervous tissue (see Sabel et al. U.S. Pat. No. 4,883,666; and Sabel et al. U.S. patent application Ser. No. 07/407,930.). It also is possible to use drug carrier systems such as liposomes, erythrocyte ghosts, antibody-conjugates, and monoclonal antibody conjugates. In accordance with this embodiment of the invention, so-called "stealth" lipids, such as phosphatidylinositol, monosialoganglioside, or sulfogalactosylceramide can be used to form the liposomes containing the aforementioned antibodies and antibody conjugates.

The segments of NTP may be conjugated with an antibody that is reactive with a transferrin receptor, as disclosed in U.S. Pat. Nos. 5,182,107 and 5,154,924. Transferrin receptors are located on brain capillary endothelial cells, which thus transport a drug, such as nerve growth factor, or segments of NTP, across the bbb. The segment of NTP-antibody conjugate described above can be further enhanced by providing cationized antibodies with a specific isoelectric point, as disclosed in U.S. Pat. No. 5,004,697 and WO 89/01343.

Another embodiment of the invention encompasses creating chimeric peptides to which the active segments of NTP are conjugated, as disclosed in U.S. Pat. No. 4,801,575. The chimeric peptide preferably is histone, which is capable of crossing the bbb by transcytosis, as disclosed in U.S. Pat. No. 4,902,505. A further embodiment of the invention includes providing the segments of NTP together with the reduced, biooxidizable lipoidal form of a dihydropyridine reaction-pyridine salt redox carrier such as dopamine, as disclosed in U.S. Pat. Nos. 4,880,816, 5,187,158, and 5,017,566.

Another approach also can be taken to deliver the segments of NTP to the brain. This can be done by chemically disrupting the bbb and then using viruses to deliver the segments of NTP across the bbb, as disclosed in U.S. Pat. No. 4,866,042. Here, it is preferred that a corrective genetic material is incorporated into a virus and the virus is then injected into the bloodstream. Yet another carrier system that can be used to deliver the segments of NTP across the bbb is the use of liposomes, as disclosed by F. D. Collins and R. C. Thompson (WO 91/04014). Here, liposomes preferably are targeted to specific endogenous brain transport systems that transport specific ligands across the bbb. Surfactant coated nanoparticles also can be used as a drug carrier (or targeting molecule) for the segments of NTP of the invention in order to enhance the penetration thereof across the bbb, as disclosed in U.S. Pat. No. 6,117,454.

Another approach is to use L-amino acid oxidase to reduce the plasma level of the segments of NTP to allow transport of the segments of NTP across the bbb. Such an approach is described in more detail in U.S. Pat. No. 5,695,751, the disclosure of which is incorporated by reference herein in its entirety.

Another approach in accordance with the present invention is to administer compositions comprising the segments of NTP locally. Devices useful in administering compositions to an internal portion of the brain are described in, for example, U.S. Pat. No. 5,800,390, the disclosure of which is incorporated by reference herein in its entirety. Sustained release, solid preparations and semi-solid preparations can be administered directly to brain tissue. Such administration can be accomplished by inserting a needle-like member of such an intracerebral device that is optionally implanted in the head so that a distal end of the guide is positioned at a site of administration.

A preferred composition of the present invention for administration to a mammal suffering from a condition associated with cell death and/or tissue necrosis contains the segments of NTP, and a component that enables the segments of NTP to cross the bbb. Other preferred compositions of the present invention include a gene that expresses the segments of NTP and a component that enables the gene to cross the bbb. An additional preferred composition of the present invention includes a vaccine that induces expression of the segments of NTP and a component that enables the vaccine to cross the bbb.

It is preferred in the present invention that the amount of segments of NTP that contacts the live tissue be an amount sufficient to inhibit, prevent, and/or ameliorate cell death and/or tissue necrosis. The specific amount can be determined by those skilled in the art, using the guidelines provided herein. It is preferred that enough segments of NTP be administered to reduce cell death or tissue necrosis by more than 50%, when compared to a control where no segment of NTP is present and cell death goes unchecked. More preferably, the segments of NTP are administered to reduce cell death or tissue necrosis by more than 60%, even more preferably by more than 70%, and most preferably by more than 75%, when compared to a control where no segment of NTP is present and cell death or tissue necrosis goes unchecked.

Such an amount will invariably depend on the particular type of tissue, the segments of NTP used, as well as the amount of NTP or other molecular target. Using the methods disclosed in any of the aforementioned U.S. Pat. Nos. 5,948,634, 5,948,888, 5,830,670, and 6,071,705, one can estimate the relative amount of NTP or other molecular target present, and then conduct a series of in vitro experiments using mammalian tissue obtained from various sources, such as any of those disclosed in the aforementioned U.S. patents, determining the amount of NTP or other molecular target in the tissue, and then determining the requisite amount of segments of NTP that is required to obtain the requisite degree of cell death or tissue necrosis prevention (i.e., preferably by more than 60% when compared to a control). Skilled artisans are capable of carrying out these experiments using techniques known in the art, as well as using the guidelines provided herein.

The amount of segments of NTP to be administered to the mammal then can readily be determined based on the body weight of the mammal, and the expected delivery amount to the tissue. The amount of segments of NTP that will be expected to be delivered to the brain tissue of a mammal will depend on the particular mechanism that is employed to render the segments of NTP capable of crossing the bbb. The same holds true for administration of genes that express the segments of NTP or for the administration of vaccines that induce expression or production of the segments of NTP. Again, those skilled in the art are capable of determining the appropriate dose of gene, vaccine, segments of NTP to administer to a mammal using the techniques described in the aforementioned patents that are incorporated by reference herein in their entirety, and by using the guidelines provided therein and herein.

The following examples are provided to illustrate the present invention. It should be understood, however, that the invention is not to be limited to the specific conditions or details described in these examples.

EXAMPLE 1

This example demonstrates cell death in live tissue (in vivo) due to the presence of AD7C-NTP.

AD7C-NTP was obtained in accordance with the procedures outlined in any one of U.S. Pat. Nos. 5,948,634, 5,948,888, 5,830,670, and 6,071,705.

Eight normal rats were injected in the skin and subcutaneously, each in 3 different foci, with purified recombinant AD7C-NTP in saline at concentrations of 0.1-1.0 µg/mL delivered from plastic syringes through stainless steel 26 gauge needles.

The animals were observed for 24 hours and painlessly sacrificed at 24 hours. The 24 individual foci of infiltration were excised, fixed in 10% formalin, embedded in paraffin, and stained and examined by standard histopathological methods.

Similar groups of control rats were injected with (1) bovine serum albumin in saline, (2) normal human serum, and (3) physiological saline, and examined and sacrificed as above, with the excised foci of injection treated as above.

Injection of AD7C-NTP in all examples produced acute necrosis of tissue at the injection sites. The necrosis is evident in muscle tissue, subcutaneous connective tissue, and dermis at the sites where the AD7C-NTP was injected. At 24 hours, cells appear pale, shrunken, and necrotic, and there is infiltration with inflammatory cells. The necrosis correlates with the areas of injection and does not appear to spread far beyond the site of injection.

Controls showed no evidence of necrosis or cell loss. Control injections had mild to minimal acute inflammation and focal microhemorrhages from the needles.

EXAMPLE 2

The purpose of this example was to identify several Harlil sequences of the AD7C-NTP neural thread protein and determine their reactivity with AD7C-NTP.

The following Harlil sequences were synthesized (Synpep, Dublin Calif.) and conjugated to maleimide activated Rabbit IgG (Jackson Immunoresearch, West Grove Pa.) and assessed for their NTP immunoreactivity. A linker was added, which was a repetition of the protein sequence occurring before and after the 90-96H H A R L C L (SEQ ID NO: 19) sequence of AD7C-NTP.

| 1. | (NTP-1) | L H A R L C L A N F C G R N R V<br>(SEQ ID NO: 33) |
| 2. | (NTP-2) | L A R L C L A N F C G N N N V<br>(SEQ ID NO: 34) |
| 3. | (NTP-3) | C A R Y R T G H H A R L M<br>(SEQ ID NO: 35) |
| 4. | (NTP-4) | H H A R L P L A N F C G<br>(SEQ ID NO: 36) |

-continued

| 5. | (NTP-5) | R T G H H A R L C L A N F C<br>(SEQ ID NO: 37) |
| 6. | (NTP-6) | C E S A R Y R T G H H A R L C<br>(SEQ ID NO: 38) |
| 7. | (NTP-7) | D N T H H A R L I L<br>(SEQ ID NO: 39) |
| 8. | (NTP-8) | S H U A R L I L<br>(SEQ ID NO: 40) |

Conjugation to carrier proteins was through a cysteine. Thus, peptides NTP-1 and NTP-2 produced mixed conjugate results because there were more than one cysteine residue. Therefore, for peptides NTP-5 and NTP-6, the secondary cysteine was blocked with Acetamido Methyl ($C_3H_6NO$) (ACM).

The location of the identified sequences in the AD7C-NTP sequence can be seen in FIG. 1. As mentioned above, homologues, derivatives, mimetics and variants of the Harlil peptides are also encompassed by the scope of the invention. For construction of the homologous peptides of this example, homologous amino acids were used. The substitution criteria used were charge and/or size. Thus, the choice to substitute methionine for cysteine in NTP peptide 3 was based on overall similarity between these two amino acids and the desire to remove a reactive cysteine from this particular stretch of amino acids. The choice to substitute proline for cysteine was an attempt to see if this would mimic the conformational form of the peptide when it was in the protein and the cysteine was in disulfide linkage.

Other changes known to persons of skill in the art to affect or study affinity interactions include, but are not limited to, for example, interchanging leucine with other hydrophobic amino acids, such as isoleucine, valine, alanine or glycine; interchanging acidic amino acids or basic amino acids; interchanging histidine with phenylalanine to determine the effect of charge vs spatial; interchanging asparagine with aspartic, or glutamine with glutamic, to evaluate the effect of charge vs spatial; and interchanging serine with threonine, threonine with cysteine, aspartic with glutamic, arginine with lysine or histidine, and tyrosine with tryptophan or phenylalanine. The changes introduced to the flanking sequences were done to render the peptide less basic or hydrophobic

EXAMPLE 3

This example demonstrates preventing and/or inhibiting necrosis of live tissue (in vivo) by administering a segment of NTP or homologue, variant, mimetic or derivative thereof that binds NTP to tissue that contains NTP.

AD7C-NTP was obtained as described above in Example 1.

The Harlil sequences NTP-1, NTP-3, and NTP-7 prepared in accordance with Example 2 above were used in this example.

Recombinant AD7C-NTP samples 100 ng/mL-10 µg/mL were incubated at room temperature for 5 minutes to one hour with the aforementioned Harlil sequences and then injected into rats as described in Example 1.

Alternatively, a solution of the Harlil sequence was made up in concentrations ranging from 1 microgram/mL to 1 milligram/mL. Solutions containing the recombinant AD7C-NTP also were made up as described above, without the addition of the Harlil sequence. The animals were injected with about 100 microliters of the AD7C-NTP solution, and with about 100 microliters of the Harlil solution.

The animals were observed for 24 hours and painlessly sacrificed at 24 hours. The 24 individual foci of infiltration were excised, fixed in 10% formalin, embedded in paraffin, and stained and examined by standard histopathological methods.

Similar groups of control rats were injected with (1) AD7C-NTP alone as described in Example 1, (2) bovine serum albumin in saline, (3) normal human serum, and (4) physiological saline, and examined and sacrificed as above, with the excised foci of injection treated as above.

The control injections of AD7C-NTP alone produced tissue necrosis, as described in Example 1. Control injections of bovine serum albumin (BSA), normal human serum, and physiological saline all showed no evidence of necrosis or cell loss. The above control injections had mild to minimal acute inflammation and focal microhemorrhages from the needles.

The AD7C-NTP samples that were injected together with each of the Harlil sequences NTP-1, NTP-3, and NTP-7 showed over 95% reduction in tissue necrosis, when compared to the control samples injected with AD7C-NTP alone. There were occasional focal nodules of inflammatory cell foci with micronodule formation which appeared to possibly be aggregation of AD7C-NTP and the Harlil sequence. The overall tissue injury was reduced by >95% by administration of the segment of NTP (or Harlil sequence), when compared to controls that were injected only with AD7C-NTP.

While the invention has been described in detail with reference to particularly preferred embodiments and examples, those skilled in the art will appreciate that various modifications may be made to the invention without departing from the spirit and scope thereof.

What is claimed is:

1. A composition comprising a Harlil peptide and a component that enables the Harlil peptide to cross the blood-brain barrier, wherein the Harlil peptide is selected from the group consisting of: H A R L I L (SEQ ID NO: 18); T H A R L I L (SEQ ID NO:22); D N T H H A R L I L (SEQ ID NO:39); and S H H A R L I L (SEQ ID NO: 40).

2. The composition of claim 1 wherein the component that enables the Harlil peptide to cross the blood-brain barrier is selected from the group consisting of cytokines, transferrin, encephalins, endorphins, osmotic agents, controlled release polymer, liposomes, erythrocyte ghosts, antibody-conjugates, monoclonal antibody conjugates, chimeric peptides, viruses, and surfactant coated nanoparticles.

* * * * *